US006958328B2

(12) United States Patent
Heintzelman et al.

(10) Patent No.: US 6,958,328 B2
(45) Date of Patent: Oct. 25, 2005

(54) ARYLINDENOPYRIDINES AND RELATED THERAPEUTIC AND PROPHYLACTIC METHODS

(75) Inventors: Geoffrey R. Heintzelman, Annandale, NJ (US); Kristin M. Averill, High Bridge, NJ (US); John H. Dodd, Stockton, NJ (US)

(73) Assignee: Ortho-McNeil Pharmaceutical, Inc, Raritan, NJ (US)

( * ) Notice: Subject to any disclaimer, the term of this patent is extended or adjusted under 35 U.S.C. 154(b) by 138 days.

(21) Appl. No.: 10/123,389

(22) Filed: Apr. 16, 2002

(65) Prior Publication Data

US 2003/0212089 A1 Nov. 13, 2003

Related U.S. Application Data

(60) Provisional application No. 60/284,465, filed on Apr. 18, 2001.

(51) Int. Cl.⁷ ..................... A61K 31/438; C07D 221/16
(52) U.S. Cl. ....................................... 514/210; 546/111
(58) Field of Search .......................... 546/111; 514/210

(56) References Cited

U.S. PATENT DOCUMENTS 6,063,788 A * 5/2000 Brandes et al. ............. 514/290

FOREIGN PATENT DOCUMENTS

| EP | 0825185 A1 | 2/1998 |
|---|---|---|
| JP | 2001 139556 A | 4/2001 |
| WO | WO 94/09002 A1 | 4/1994 |
| WO | WO 99/03846 A1 | 1/1999 |
| WO | WO 00/42019 A1 | 7/2000 |
| WO | WO 00/68230 A1 | 11/2000 |
| WO | WO 01/21621 A1 | 3/2001 |
| WO | WO 93 08167 A | 4/2001 |
| WO | WO 01 62233 A | 8/2001 |
| WO | WO 02 085894 A | 10/2002 |
| WO | WO 03 088963 A | 10/2003 |

OTHER PUBLICATIONS

Ulrich Rose, 1990, "5–oxo–1,4–dihydroindenopyridines: calcium modulators . . ", CAS:113:78100.*
Copy of PCT Search Report dated Aug. 27, 2002, for PCT International Application No. PCT/US02/11823.
Afsah, E.M. et al.: "Introduction of some phamaceuticially active heterocycles into the benzylic moiety of 2–benzyl–1, 3–indandione"; Pharmazie 45 (1990), H.4, pp. 255–257.
Bocker, R.H. et al.: "Oxidation of 4–Aryl–and 4–Alkyl–Substituted 2,6–Dimethyl–3,5–bis(alkoxycarbonyl)–1,4–dihydropyridines by Human Liver Microsomes and Immunochemical Evidence for the Involvement of a Form of Cytochrome P–450"; J. Med. Chem. 1986, 29, pp. 1596–1603.

Bradley, G. et al.: "2,3–Dihydroquinolin–4(1H)–ones. Part I. Halogen–substituted 2,3–Di–hydroquinolin–4(1H)–ones and their 1–(2–Acylethyl) Derivatives"; J. Chem. Soc., Perkin Trans. 1, 1972, pp 2019–2023.
Bullington, J.L. et al.: "The Development of NOvel and Selective p56ck Tyrosine Kinase Inhibitors[1]"; Bioorg. Med. Chem. Lett. 1998, 8, pp. 2489–2494.
Chatterjea, J.N. et al.; "Synthesis in the 4–Azafluorene Group. Part III"; J. Indian Chem. Soc., vol. LV, 1978, pp. 149–153.
Gorlitzer, K. et al.: "Indeno[1,2–b]pyridin–4–yl–amine[3]"; Pharmazie 52 (1997) 7, pp. 504–510.
Jursic, B.S. et al.: "A Simple Preparation of Amides from Acids and Amines by Heating of their Mixture"; Synthetic Comm. 1993, 23, pp. 2761–2770.
Kobayashi, T. et al: "Novel 2–Amino–1,4–dihydropyridine Calcium Antagonists. I. Synthesis and Antihypertensive Effects of 2–Amio–1,4–dihydropyridine Derivatives Having Nitroxyalkoxycarbonyl Groups at 3– and/or 5–Position"; Chem. Pharm. Bull. 1995, 43, pp. 788–796.
Li, L. et al.: "CD3– and CD28–Dependent Induction of PDE7 Required for T Cell Activation"; Science, Feb. 5, 1999, vol. 283, pp. 848–851.
Lusis, V. et al.: "Synthesis and Isomerization of 1H–4,4a,5, 9b–Tetrahydroindeno–[1,2–b]pyridines"; Tetrahedron 1991, vol. 47, No. 35, pp. 7429–7436.
Martinez, A. et al.: "Benzyl Derivatives of 2,1,3–Benzo– and Benzothieno[3,2–a]thiadiazine 2,2–Dioxides: First Phosphodiesterase 7 Inhibitors"; J. Med. Chem. 2000, 43, pp. 683–689.
Ogawa, T. et al.: "Synthesis and Configurational Assignment of Methyl 3Nitrooxypropyl 1,4–Dihydro–2, 6–dimethyl–4–(3–nitrophenyl)pyridine–3,5–dicarboxylate"; J. Chem. Soc. Perkin Trans. 1 1993, pp. 525–528.
Omuaru, V.O.T.: "Reactions of cyclic anhydrides with aromatic primary amines: Part 3—Synthesis of novel 3–(N–arylcarbamoyl)– and 3–(N–naphthylcarbamoyl)carboxylic acids"; Indian J. of Chem. Sect. B. 1998, 37, pp. 814–816.
Petrow, V. et al.: "New Synthesis of Heterocyclic Compounds. Part X. 4–Azafluorenones", JCS, 1949, pp. 2134–2139.

(Continued)

*Primary Examiner*—Rita Desai
*Assistant Examiner*—Robert Shiao

(57) ABSTRACT

This invention provides novel arylindenopyridines of the formula:

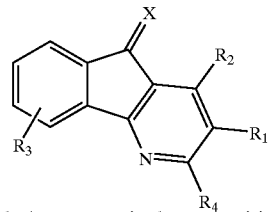

, and pharmaceutical compositions comprising same, useful for treating disorders ameliorated by reducing PDE activity in appropriate cells. This invention also provides therapeutic and prophylactic methods using the instant pharmaceutical compositions.

35 Claims, No Drawings

OTHER PUBLICATIONS

Reddy, A.S. et al.: "A convenient method for the preparation of hydroxamic acids"; Tetrahedron Letters 41 (2000), pp. 6285–6288.

Rose, U.: "5–Oxo–1,4–dihydroindenopyridines: Calcium Modulators with Partial Calcium Agonistic Activity"; J. Heterocyclic Chem., 27, (1990), pp. 237–242.

Sausin'sh, A. et al.: "Methods for the Synthesis of 4–Pyrazolyl– and 4–Pyridyl–5–Oxo–1,4,5,7–Tetrahydrofuro[3,4–b]Pyridines"; Chem. of Heterocyclic Compounds, vol. 31, No. 7, 1995, pp. 841–846.

Vanden Eynde, J.J. et al.: "Old Reagents, New Results: Aromatization of Hantzsch 1,4–Dihydropyridines awith Manganese Dioxide and 2,3–Dichloro–5,6–dicyano–1,4–benzoquinone."; Tetrahedron vol. 51, No. 23 (1995), pp. 6511–6516.

Vigante, B. et al.: Latv. PSR Zinat. Akad. Vestis, Kin. Ser. 1980, p. 707–175.

Vigante, B.A. et al.: "Infrared Absorption of 4,5–Dihdroindeno[1,2–b]Pyridines"; Chem. Het. Compounds, 25(5) 1989, pp. 524–527.

Weissman, S.A. et al.: "Efficient Synthesis of N–Arylpiperazinones via a Selective Intramolecular Mitsunobu Cyclodehydration"; Tetrehedron Lett. 1998, 39, pp. 7459–7462.

Zandersons, A. et al.: "Synthesis of 5–Oxoindeno[1,2–b] Pyridinium Salts"; Chem. Het. Compounds 22(1), 1986, pp. 73–76.

Zimmer, H. et al.: "Substituted y–Lactones. 28.[1] 3–(Phenylmethylene)–2,4(3H,5H)–furandiones"; J. Org. Chem. vol. 43, No. 8, 1978, pp. 1541–1544.

Chemical Abstracts, vol. 59, No. 6, Sep. 1963; XP–002211132.

El–Tawell F. M. A. et. al.: "Synthetic Routes to Fluorenone, Indenopyiroine, 4H–Naphthoa2, 1–Bupyrans and Pyridine Derivaties", Bolettino Chimico Farmaceutico, Societa Editoriate Farmaceutica, Milano, Italy, vol. 140, No. 5, 2001, pp. 306–310, XP009025181, ISSN: 0006–6848 See compound 14.

Goerlitzer K. et al: "IndenoA1, 2– Dupyrimidin– 4–YL–Amine IndenoA1, 2upyrimidin–4–YL–Amines" Pharmazie, Veb Varleg Volk Und Gesundheit. Berlin, DD vol. 52, No. 9, 1997 pp. 670–672, XP001179310, ISSN: 0031–7144 see compounds 3, 6–8 and whole article, especially 2.2.1.

Burger K. et. al. "Trifluormethyl–Substituierte Pryimidine Aus Enaminen Und Trifluoracetonitril Trifluoromethyl–Substituted Pyrimidines from Enamines and Trifluoroacetonitrile" Liebigs Annalen Der Chemie, Verlag Chemie GMBH Weinheim, DE, vol. 5, 1964, pp. 991–1002 XP001179309 ISSN:0170–2041 see compund 18a.

Demerac S. et. al., "5H–IndenoA1, 2–Dupyrumidin–5–Ones" Austrailian Journal of Chemistry, XX, XX, vol. 25, 1972, pp. 2651–2657, XP009025111 issn: 0004–9425 see compounds 5a–5e and 9–11.

Augustin, M.: "Synthese Und Reaktionen Von 2–Abis–(Alklthio)–Methlidenu–Indan–1, 3–Dionen Synthesis and Reactions of 2–Abis–(Alkylthio)–Methlidenu–Indan–1, 3–Dion", Journal Fuer Praktische Chemie, Wiley Wein-Heim, DE, vol. 321, No. 2, 1979, pp. 205–214, XP009025100, ISSN: 1436–9966, see 11b, p. 212 and 11c, p213.

N El–Rayyes; "Heterocycles. 14. Sythesis of 5H–Indenopyrumidines" J. Chem. Eng. Data, vol. 32, 1967, pp. 481–483, XP002270517 see formula VII, f,h,j, Va–k.

Kappe C. O. et. al. "Sythesis and Reactions of Biginelli–Compounds. Part I" Journal of Heterocyclic Chemistry, Heterocorporation Provo, US, Jan. 1989, pp. 55–64, XP002952094, ISSN: 00220152X, see compound 29a.

A. Rosowsky; "One Step Sythesis of Nove 2, 4–Diaminopyrumudube Antifolates" J. Heterocyclci Chemistry vol. 36, 1999, pp. 723–728, XP002270518 see 20(14).

Kandeel, E.M. et. al.: "Sythnesis of New 1,2–Dihydro–4–Amino–2–Thioxo–5H–Indeno 1,2–D Pyrimidin–5–One Derivaties" Pakistan Journal of Scientific and Industrial Research, XX, XX, vol. 29, No. 6, Dec. 1988 pp. 424–426, XP009025187 ISSN: 0030–9885 see V1a, V1b, Va, Vb.

PCT Search Report dated Jan. 3, 2004, for PCT Appl. No. PCT/US03/31471.

PCT Search Report dated Jan. 23, 2003, for corresponding PCT application number PCT/US02/30825.

Database CHEMCATS 'Online (Feb. 11, 2002), Interbioscreen Compound Library:2002:3027027, XP002220645.

Database CHEMCATS 'Online' (Jan. 21, 2002), Ambinter: Exploratory Library: 2002:2845045, 2002: XP00222646.

Database CHEMCATS 'Online' (Jan. 21, 2002), Ambinter: Exploratory Library: 2002:1552297, XP002220647.

Database CHEMCATS 'Online' (Jan. 15, 2002), Bionet Research: 2001:2494341, 2001:2494321, XP002220648.

Database CHEMCATS 'Online' (Jul. 1, 2001), Compounds for Screening: 2001:1603530, XP002220649.

Database CA 'Online' Chemical Abstracts Service, Columbus, OH, US; Kandeel, Ez–El–Din M.: "Synthesis of some new functionalized pyridines, 5–oxoindeno'1, 2–blpyridines and related compounds of potential pharmaceutical interest" 136:200063 XP002220650 abstract & Mansura Science Bulletin, A; Chemistry (2000), 27(2), 35–49.

Database CA 'Online' Chemical Abstracts Service, Columbus, OH, US; Sausins, A. et al: "Methods of synthesis of 4–(pyridyl)–5–oxo–1, 4, 5, 7–tetrehyrofuro'3, 4–blpyridines" 124:202067 XP002220651 & Khimiya Geterotsiklicheskikh Soedinenii (1995), (7), 966–72.

Database CA 'Online' Chemical Abstracts Service, Columbus, OH, US: Geies, Ahmed A. et al: "Synthesis of indeno'1, 2–blpyridines and indeno'1 , 2–blthleno'3, 2–elpyridines" 128:244011 XP002220652 & Bulletin of the Polish Academy of Sciences, Chemistry (1997), 45(4), 381–390, 2 plates.

Database CA 'Online' Chemical Abstracts Service, Columbus, OH, US; Zandersons, A. et al: "Synthesis of substituted 5–oxoindeno'1, 2–blpyridinium salts" 105:208733 XP002220654 & Khimiya Geterotsiklicheskikh Soedinenii (1986), (1), 88–90.

Database CA 'Online' Chemical Abstracts Service, Columbus, OH, US; Stankevich, E. et al: "Polynuclear heterocyclic compounds. XIII. New derivatives of 9, 11–dioxo–10–phenyl–11H–indeno'1, 2–bltetrahydroquinoline" 59:35503 XP002220655 & Latvijas Psr Zinatnu Akad. Vestis, Kim. Ser. (1962), (No. 2), 283–6.

Database CA 'Online' Chemical Abstracts Service, Columbus, OH, US; Vanags, G. et al: "Polynuclear heterocyclic compounds. VI. 4,6 –Diphenyl—2,3—(CO)—benzoylenepyridine" 58:14816 XP0002220656 & Zh. Obshch. Khim. (1962), 32, 1151–9.

Database CA 'Online' Chemical Abstracts Service, Columbus, OH, Vigante, B. et al: "Ethyl esters of 1, 4–dihydropyridine–3, 5–di–and 2–methyl–4–aryl–5oxo–4, 5 dihydro–1H–indeno'1,2–b]pyridine–3–carbothionic acids" 101:6372 XP002220657 & Khim. Geterotsikl. Soedin. (1984), (2), 210–16.

Database CA 'Online' Chemical Abstracts Service, Columbus, OH, Vigante, B. et al: "Infrared absorption of 4, 5–dihydorindeno'1,2–b]pyridines" 112:97907 XP002220658 & Khimlya Geterotsiklicheskikh Soedinenii (1989), (5), 629–32.

Database CA 'Online' Chemical Abstracts Service, Columbus, OH, Zandersons, A. et al: "Synthesis of substituted 5–oxoindeno'1, 2–b]pyridinium salts" 105:208733 XP0002220659 & Khimiya–Geterotsiklicheskikh Soedinenil (1986), (1), 88–90.

Database CA 'Online' Chemical Abstracts Service, Columbus, OH, Mucsenietce, D. et al: "Reduction and basic hydrolysis of 5–oxoindeno'1, 2–b]pyridinium salts" 107:236463 XP002220661 & Khimiya Geterotsiklicheskikh Soedinenii (1987), (1), 86–9.

Database CA 'Online' Chemical Abstracts Service, Columbus, OH Zandersons, A. et al: "Synthesis of substituted 5–oxoindeno'1, 2–b]pyridinium salts" 105:208733 XP002220662 & Khimya Geterotsiklicheskikh Soedinenii (1986), (1), 88–90.

Database CHEMCATS 'Online' (Jul. 9, 2002) Interchim Intermediats: 2002:2525250 and other XP002220663.

Database CHEMCATS 'Online' (Jul. 9, 2002) Interchim Intermediats: 2002:2403473,–3487,–3488,–3489 and 2002:2548348 XP002220664.

Database CHEMCATS'Online' (Jul. 9, 2002) Interchim Intermediats: 2002:3011492 to 2002:3011513 XP002220665.

Ascherio, A. et al: "Prospective Study of Caffeine Consumption and Risk of Parkinson's Diesease in Men and Women"; Annals of Neurology, 2001, 50, pp. 56–63.

Chen, J.F. et al.: "Neuroprotection of Caffeine and $A_{2A}$ Adenosine Receptor Inactivation in a Model of Parkinson's Disease"; J. of Neuroscience, 2001, vol. 21 RC143, pp. 1–6.

Chen, W. et al.: "A Colorimetric Assay for Measuring Activation of $G_a0G_q$–Coupled Signaling Pathways"; Analytical Biochemistry, 1995, 226, pp. 349–354.

Ferre, S. et al.: "Stimulation of high–affinity adenosine $A_2$ receptors decreases the affinity of dopamine $D_2$ receptors in rat striatal membranes"; Proceedings of the Nat'l Academy of Sciences of the USA, 1991, 88, pp. 7238–7241.

Fink, J.S. et al.: "Molecular cloning of the rat $A_2$ adenosine receptor: selective co–expression with $D_2$ dopamine receptors in rat striatum"; Molecular Brain Research, 14 (1992), pp. 186–195.

Gessi, S. et al.: "$A_{2A}$adenosine receptors in human peripheral blood cells"; British J. of Pharm., 2000, 129, pp. 2–11.

Ikeda, K. et al.: "Neuroprotection by adenosine $A_{2A}$ receptor blockade in experimental models of Parkinson's disease"; J. of Neurochemistry, 2002, 80, pp. 262–270.

Impagnatiello, F. et al.: "Adenosine receptors in neurological disorders"; Emerging Therapeutic Targets, 2000, 4, pp. 635–664.

Mally, J. et al.: "Efficacy of an adenosine antagonist, theophylline, in essential tremor: comparison with placebo and propranolol"; J. of the Neurological Sciences, 1995, 132, pp. 129–132.

Rosin, D.L. et al.: "Immunohistochemical Localization of Adenosine $A_{2A}$ Receptors in the Rat Central Nervous System"; The J. of Comparative Neurology, 1998, 401, pp. 163–186.

Salim, H. et al.: "Activation of Adenosine $A_1$ and $A_{2A}$ Receptors Modulates Dopamine $D_2$ Receptor–Induced Responses in Stably Transfected Human Neuroblastoma Cells"; J. of Neurochemistry, 2000, 74, pp. 432–439.

Stiles, G. et al.: "Adenosine Receptors"; The J. of Biological Chem., 1992, vol. 267 No. 10, pp. 6451–6454.

Varani, K. et al.: "Pharmacological and biochemical characterization of purified $A_{2A}$ adenosine receptors in human platelet membranes by [$^3$H]–CGS 21680 binding"; British J. of Pharamcology, 1996, 117, pp. 1683–1701.

* cited by examiner

ARYLINDENOPYRIDINES AND RELATED THERAPEUTIC AND PROPHYLACTIC METHODS

CROSS-REFERENCE TO RELATED APPLICATIONS

This application claims the benefit under 35 U.S.C. §119 (e) of provisional application Ser. No. 60/284,465, filed on Apr. 18, 2001 which is incorporated herein by reference.

FIELD OF THE INVENTION

This invention relates to novel arylindenopyridines and their therapeutic and prophylactic uses. Disorders treated and/or prevented using these compounds include inflammatory and AIDS-related disorders.

BACKGROUND OF THE INVENTION

There are eleven known families of phosphodiesterases (PDE) widely distributed in many cell types and tissues. In their nomenclature, the number indicating the family is followed by a capital letter that indicates a distinct gene. A PDE inhibitor increases the concentration of cAMP in tissue cells, and hence, is useful in the prophylaxis or treatment of various diseases caused by the decrease in cAMP level which is induced by the abnormal metabolism of cAMP. These diseases include conditions such as hypersensitivity, allergy, arthritis, asthma, bee sting, animal bite, bronchospasm, dysmenorrhea, esophageal spasm, glaucoma, premature labor, a urinary tract disorder, inflammatory bowel disease, stroke, erectile dysfunction, HIV/AIDS, cardiovascular disease, gastrointestinal motility disorder, and psoriasis.

Among known phosphodiesterases today, PDE1 family are activated by calcium-calmodulin; its members include PDE1A and PDE1B, which preferentially hydrolyze cGMP, and PDE1C which exhibits a high affinity for both cAMP and cGMP. PDE2 family is characterized as being specifically stimulated by cGMP. PDE2A is specifically inhibited by erythro-9-(2-hydroxy-3-nonyl)adenine (EHNA). Enzymes in the PDE3 family (e.g. PDE3A, PDE3B) are specifically inhibited by cGMP. PDE4 (e.g. PDE4A, PDE4B, PDE4C, PDE4D) is a cAMP specific PDE present in T-cells, which is involved in inflammatory responses. A PDE3 and/or PDE4 inhibitor would be predicted to have utility in the following disorders: autoimmune disorders (e.g. arthritis), inflammatory bowel disease, bronchial disorders (e.g. asthma), HIV/AIDS, and psoriasis. A PDE5 (e.g. PDE5A) inhibitor would be useful for the treatment of the following disorders: cardiovascular disease and erectile dysfunction. The photoreceptor PDE6 (e.g. PDE6A, PDE6B, PDE6C) enzymes specifically hydrolyze cGMP. PDE8 family exhibits high affinity for hydrolysis of both cAMP and cGMP but relatively low sensitivity to enzyme inhibitors specific for other PDE families.

Phosphodiesterase 7 (PDE7A, PDE7B) is a cyclic nucleotide phosphodiesterase that is specific for cyclic adenosine monophosphate (cAMP). PDE7 catalyzes the conversion of cAMP to adenosine monophosphate (AMP) by hydrolyzing the 3'-phosphodiester bond of cAMP. By regulating this conversion, PDE7 allows for non-uniform intracellular distribution of cAMP and thus controls the activation of distinct kinase signalling pathways. PDE7A is primarily expressed in T-cells, and it has been shown that induction of PDE7A is required for T-cell activation (Li, L.; Yee, C.; Beavo, J. A. Science 1999, 283, 848). Since PDE7A activation is necessary for T-cell activation, small molecule inhibitors of PDE7 would be useful as immunosuppressants. An inhibitor of PDE7A would be predicted to have immunosuppressive effects with utility in therapeutic areas such as organ transplantation, autoimmune disorders (e.g. arthritis), HIV/AIDS, inflammatory bowel disease, asthma, allergies and psoriasis.

Few potent inhibitors of PDE7 have been reported. Most inhibitors of other phosphodiesterases have $IC_{50}$'s for PDE7 in the 100 μM range. Recently, Martinez, et al., (*J. Med. Chem.* 2000, 43, 683) reported a series of PDE7 inhibitors, among which the two best compounds have PDE7 $IC_{50}$'s of 8 and 13 μM. However, these compounds were only 2–3 times selective for PDE7 over PDE4 and PDE3.

Finally, the following compounds have been disclosed, and some of them are reported to show antimicrobial activity against strains such as *Plasmodium falciparum*, *Candida albicans* and *Staphylococcus aureus* (Gorlitzer, K.; Herbig, S.; Walter, R. D. *Pharmazie* 1997, 504):

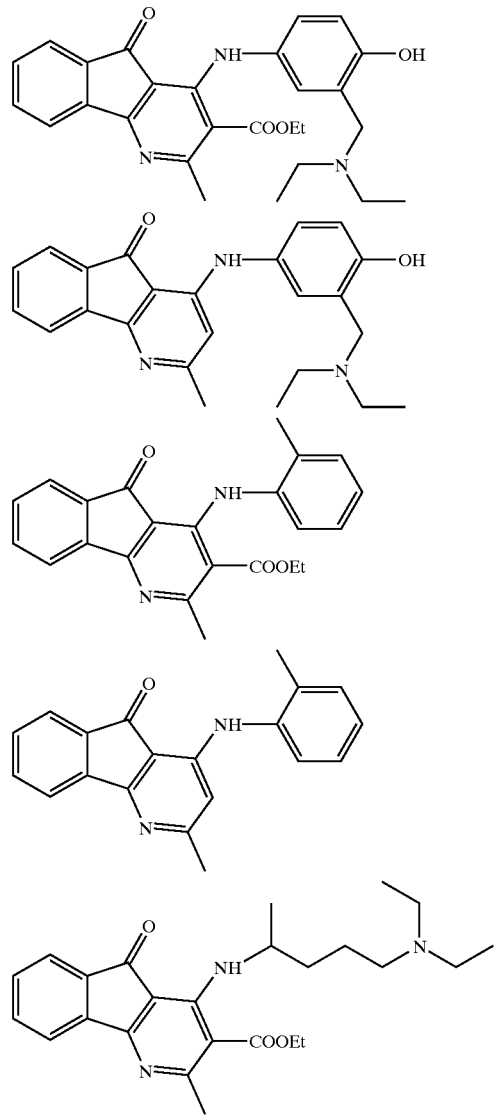

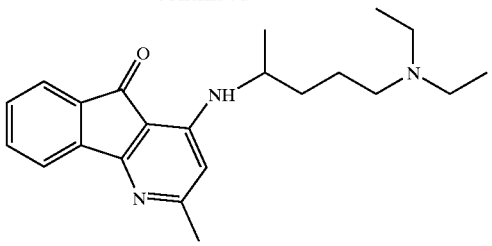

SUMMARY OF THE INVENTION

This invention provides a compound having the structure of Formula I

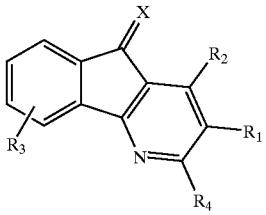

Formula I or a pharmaceutically acceptable salt thereof, wherein (a) $R_1$ is selected from the group consisting of:
  (i) —$COR_5$, wherein $R_5$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, aryl, or heteroaryl or $NR_{20}R_{21}$ taken together form a heterocycle or heteroaryl;
  (ii) $COOR_6$, wherein $R_6$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, aryl, or heteroaryl or $NR_{20}R_{21}$ taken together form a heterocycle or heteroaryl;
  (iii) cyano;
  (iv) a lactone or lactam formed with $R_4$;
  (v) —$CONR_7R_8$ wherein $R_7$ and $R_8$ are independently selected from H, $C_{1-8}$ straight or branched chain alkyl $C_{3-7}$ cycloalkyl, trifluoromethyl, hydroxy, alkoxy, acyl, alkylcarbonyl, carboxyl, arylalkyl, aryl, heteroaryl and heterocyclyl;
    wherein the alkyl, cycloalkyl, alkoxy, acyl, alkylcarbonyl, carboxyl, arylalkyl, aryl, heteroaryl and heterocyclyl groups may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy or arylalkyl,
    or $R_7$ and $R_8$ taken together with the nitrogen to which they are attached form a heterocycle or heteroaryl group;

(b) $R_2$ is selected from the group consisting of optionally substituted alkyl, optionally substituted aryl, optionally substituted heteroaryl, optionally substituted heterocyclyl and optionally substituted $C_{3-7}$ cycloalkyl;

(c) $R_3$ is from one to four groups independently selected from the group consisting of:
  (i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl, heteroaryl, and heterocyclyl;
  (ii) —$NR_{10}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, aryl, heteroaryl, and heterocyclyl or $R_{10}$ and $R_{11}$ taken together with the nitrogen form a heteroaryl or heterocyclyl group;
  (iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxyalkyl, $R_{30}R_{31}N(CH_2)_p$—, $R_{30}R_{31}NCO(CH_2)_p$—, aryl, arylalkyl, heteroaryl and heterocyclyl or $R_{12}$ and $R_{13}$ taken together with the carbonyl form a carbonyl containing heterocyclyl group, wherein, $R_{30}$ and $R_{31}$ are independently selected from H, OH, alkyl, and alkoxy, and p is an integer from 1–6,
    wherein the alkyl group may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy or arylalkyl;

(c) $R_4$ is selected from the group consisting of (i) hydrogen, (ii) $C_{1-3}$ straight or branched chain alkyl, (iii) benzyl and (iv) —$NR_{13}R_{14}$, wherein $R_{13}$ and $R_{14}$ are independently selected from hydrogen and $C_{1-6}$ alkyl; wherein the $C_{1-3}$alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, aryl and heteroaryl; and (e) X is selected from S and O;
with the proviso that when $R_4$ is isopropyl, then $R_3$ is not halogen.

In an alternative embodiment, the invention is directed to compounds of Formula I wherein $R_1$, $R_3$ and $R_4$ are as described above and $R_2$ is —$NR_{15}R_{16}$ wherein $R_{15}$ and $R_{16}$ are independently selected from hydrogen, optionally substituted $C_{1-8}$ straight or branched chain alkyl, arylalkyl, $C_{3-7}$ cycloalkyl, aryl, heteroaryl, and heterocyclyl or $R_{15}$ and $R_{16}$ taken together with the nitrogen form a heteroaryl or heterocyclyl group; with the proviso that when $R_2$ is $NHR_{16}$, $R_1$ is not —$COOR_6$ where $R_6$ is ethyl.

This invention also provides a pharmaceutical composition comprising the instant compound and a pharmaceutically acceptable carrier.

This invention further provides a method of treating a subject having a disorder ameliorated by reducing PDE activity in appropriate cells, which comprises administering to the subject a therapeutically effective dose of the instant pharmaceutical composition.

Finally, this invention provides a method of preventing a disorder ameliorated by reducing PDE activity in appropriate cells in a subject, comprising administering to the subject a prophylactically effective dose of the compound of claim 1 either preceding or subsequent to an event anticipated to cause a disorder ameliorated by reducing PDE activity in appropriate cells in the subject.

DETAILED DESCRIPTION OF THE INVENTION

Compounds of Formula I are potent small molecule phosphodiesterase inhibitors that have demonstrated potency for inhibition of PDE7, PDE5, and PDE4. Some of the compounds of this invention are potent small molecule PDE7 inhibitors which have also demonstrated good selectivity against PDE5 and PDE4.

Preferred embodiments for $R_1$ are $COOR_6$, wherein $R_6$ is selected from H, optionally substituted $C_{1-8}$ straight or branched chain alkyl, optionally substituted aryl and optionally substituted arylalkyl. Preferably $R_6$ is H, or $C_{1-8}$ straight or branched chain alkyl which may be optionally substituted with a substituent selected from CN and hydroxy.

Preferred embodiments for $R_2$ are optionally substituted aryl and optionally substituted heteroaryl. Preferred substituents are from one to three members selected from the group consisting of halogen, alkyl, alkoxy, alkoxyphenyl, halo, triflouromethyl, trifluoro or difluoromethoxy, amino, alkylamino, hydroxy, cyano, and nitro. Preferably, $R_2$ is optionally substituted phenyl or napthyl or $R_2$ is

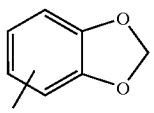

optionally substituted with from one to three members selected from the group consisting of halogen, alkyl, hydroxy, cyano, and nitro. In another embodiment of the instant compound, $R_2$ is $-NR_{15}R_{16}$.

Preferred substituents for $R_3$ include:

(i) hydrogen, halo, $C_{1-8}$ straight or branched chain alkyl, $C_{1-8}$ alkoxy, cyano, $C_{1-4}$ carboalkoxy, trifluoromethyl, $C_{1-8}$ alkylsulfonyl, halogen, nitro, and hydroxy;

(ii) $-NR_{10}R_{11}$ wherein $R_{10}$ and $R_{11}$ are independently selected from H, $C_{1-8}$ straight or branched chain alkyl, aryl$C_{1-8}$alkyl, $C_{3-7}$ cycloalkyl, carboxy$C_{1-8}$alkyl, aryl, heteroaryl, and heterocyclyl or $R_{10}$ and $R_{11}$ taken together with the nitrogen form a heteroaryl or heterocyclyl group;

(iii) $-NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxy$C_{1-8}$alkyl, aryl, arylalkyl, $R_{30}R_{31}N$ $(CH_2)_p-$, $R_{30}R_{31}NCO(CH_2)_p-$, heteroaryl and heterocyclyl or $R_{12}$ and $R_{13}$ taken together with the carbonyl form a carbonyl containing heterocyclyl group, wherein, $R_{30}$ and $R_{31}$ are independently selected from H, OH, alkyl, and alkoxy, and p is an integer from 1–6.

Particularly, $R_3$ is selected from the group consisting of

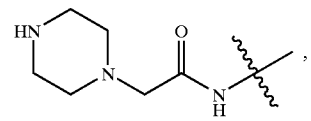

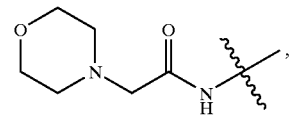

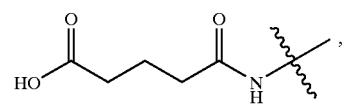

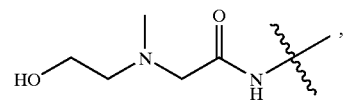

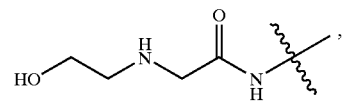

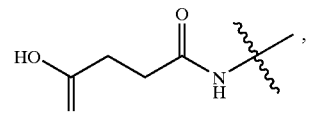

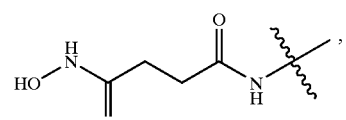

alkyl(CO)NH—, $NH_2$, and $NO_2$.

Preferred embodiments for $R_4$ include hydrogen, $C_{1-3}$ straight or branched chain alkyl, particularly methyl, and amino.

In a further embodiment of the instant compound, $R_1$ is $COOR_6$ and $R_2$ is selected from the group consisting of substituted phenyl, and substituted naphthyl or $R_2$ is $NR_{15}R_{16}$.

More particularly, $R_1$ is $COOR_6$ where $R_6$ is alkyl, $R_2$ is substituted phenyl or naphthyl or $R_2$ is $NR_{15}R_{16}$, and $R_3$ is selected from the group consisting of H, nitro, amino, NHAc, halo, hydroxy, alkoxy, or a moiety of the formulae:

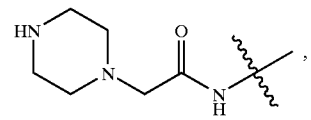

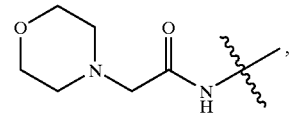

-continued

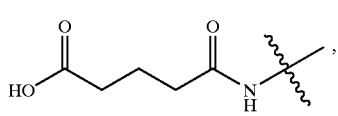

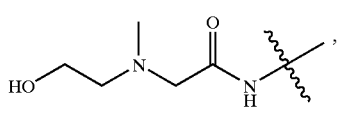

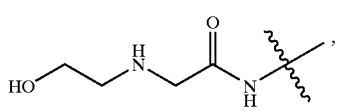

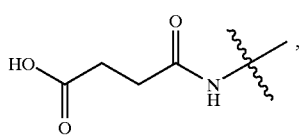

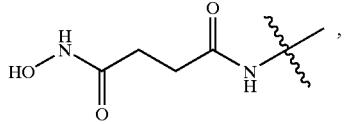

alkyl(CO)NH—, and $R_4$ is selected from hydrogen, $C_{1-3}$ straight or branched chain alkyl, particularly methyl, and amino.

In a preferred embodiment, the compound is selected from the group of compounds shown in Table 1 hereinafter.

More preferably, the compound is selected from the following compounds:

Compound 22

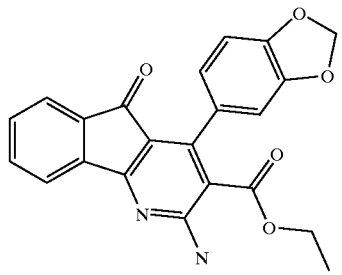

5H-indeno[1,2-b]pyridine-3-carboxylic acid, 2-amino-4-(1,3-benzodioxol-5-yl)-5-oxo-, ethyl ester Compound 24

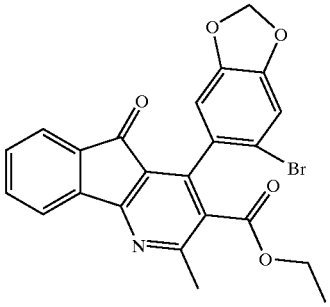

5H-indeno[1,2-b]pyridine-3-carboxylic acid, 4-(6-bromo-1,3-benzodioxol-5-yl)-2-methyl-5-oxo-, ethyl ester Compound 40

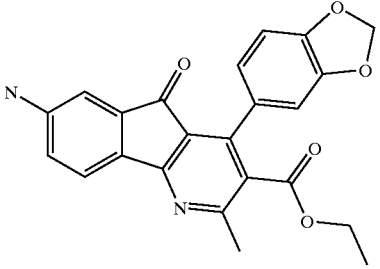

5H-indeno[1,2-b]pyridine-3-carboxylic acid, 7-amino-4-(1,3-benzodioxol-5-yl)-2-methyl-5-oxo-, ethyl ester Compound 49

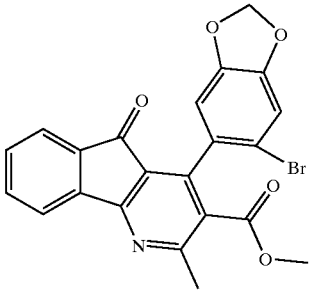

5H-indeno[1,2-b]pyridine-3-carboxylic acid, 4-(6-bromo-1,3-benzodioxol-5-yl)-2-methyl-5-oxo-, methyl ester Compound 51

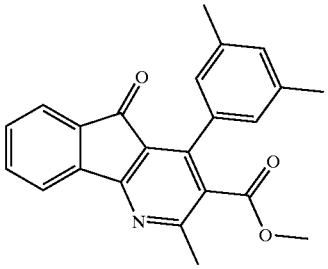

5H-indeno[1,2-b]pyridine-3-carboxylic acid, 4-(3,5-dimethylphenyl)-2-methyl-5-oxo-, methyl ester 5H-indeno[1,2-b]pyridine-3-carboxylic acid, 7-amino-4-(3,5-dimethylphenyl)-2-methyl-5-oxo-, methyl ester Compound 56

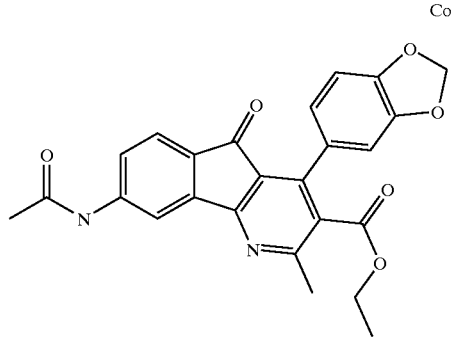

Compound 90

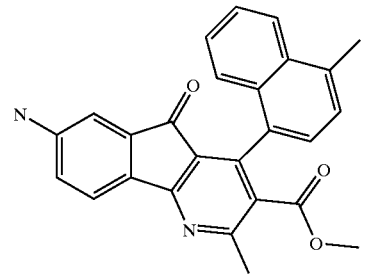

5H-indeno[1,2-b]pyridine-3-carboxylic acid, 7-amino-2-methyl-4-(4-methyl-1-naphthalenyl)-5-oxo-, methyl ester Compound 169

5H-indeno[1,2-b]pyridine-3-carboxylic acid, 8-(acetylamino)-4-(1,3-benzodioxol-5-yl)-2-methyl-5-oxo-, ethyl ester

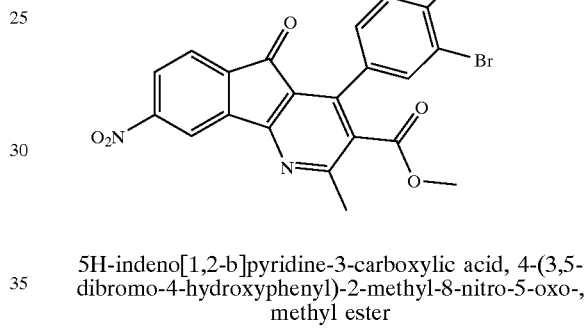

Compound 67

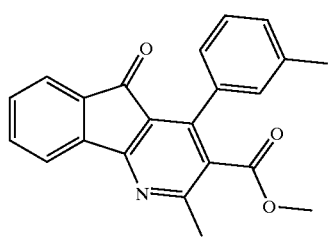

5H-indeno[1,2-b]pyridine-3-carboxylic acid, 4-(3,5-dibromo-4-hydroxyphenyl)-2-methyl-8-nitro-5-oxo-, methyl ester Compound 170

5H-indeno[1,2-b]pyridine-3-carboxylic acid, 2-methyl-4-(3-methylphenyl)-5-oxo-, methyl ester 5H-indeno[1,2-b]pyridine-3-carboxylic acid, 7,8-dichloro-4-(3,5-dibromo-4-hydroxyphenyl)-2-methyl-5-oxo-, methyl ester Compound 82

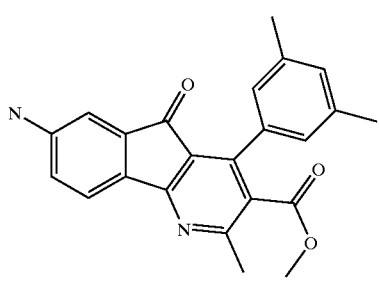

Compound 192

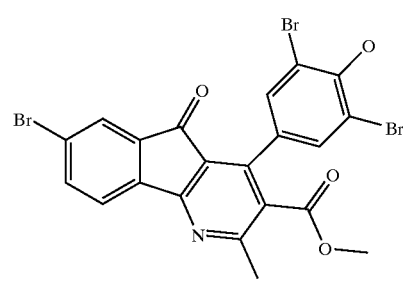

11

5H-indeno[1,2-b]pyridine-3-carboxylic acid, 7-bromo-4-(3,5-dibromo-4-hydroxyphenyl)-2-methyl-5-oxo-, methyl ester Compound 193

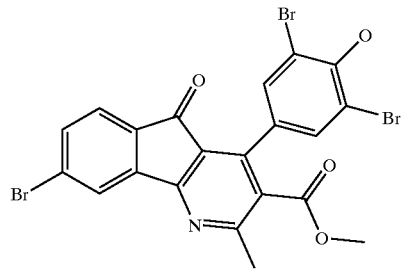

5H-indeno[1,2-b]pyridine-3-carboxylic acid, 8-bromo-4-(3,5-dibromo-4-hydroxyphenyl)-2-methyl-5-oxo-, methyl ester Compound 241

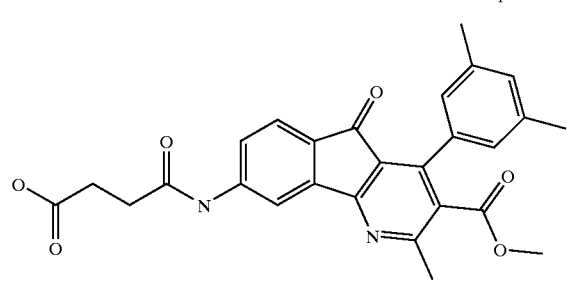

5H-indeno[1,2-b]pyridine-3-carboxylic acid, 8-[(3-carboxy-1-oxopropyl)amino]-4-(3,5-dimethylphenyl)-2-methyl-5-oxo-, methyl ester Compound 242

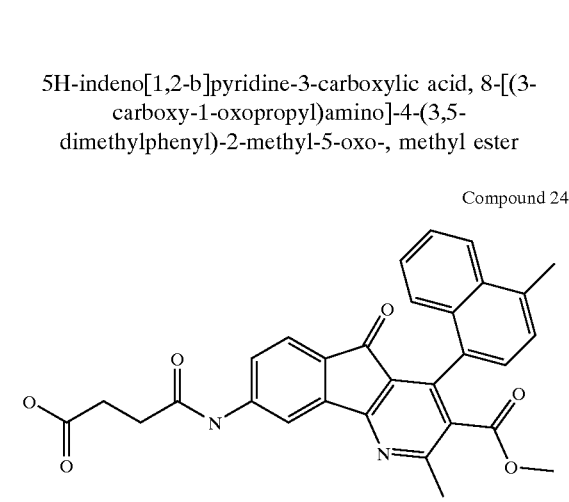

12

5H-indeno[1,2-b]pyridine-3-carboxylic acid, 8-[(3-carboxy-1-oxopropyl)amino]-2-methyl-4-(4-methyl-1-naphthalenyl)-5-oxo-, methyl ester Compound 245

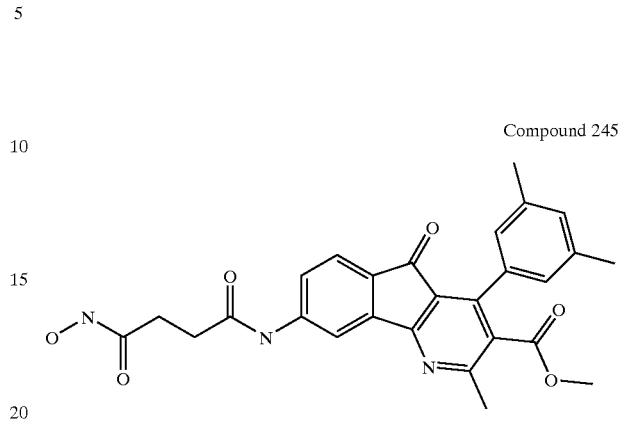

5H-indeno[1,2-b]pyridine-3-carboxylic acid, 4-(3,5-dimethylphenyl)-8-[[4-(hydroxyamino)-1,4-dioxobutyl]amino]-2-methyl-5-oxo-, methyl ester Compound 250

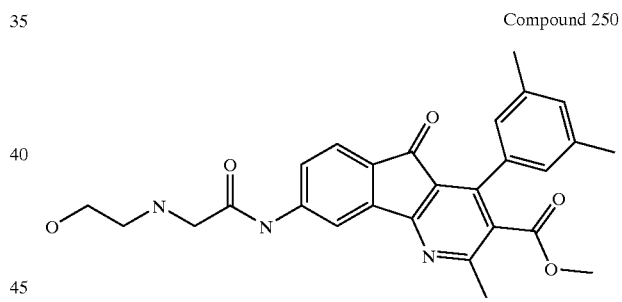

5H-indeno[1,2-b]pyridine-3-carboxylic acid, 4-(3,5-dimethylphenyl)-8-[[[(2-hydroxyethyl)amino]acetyl]amino]-2-methyl-5-oxo-, methyl ester Compound 251

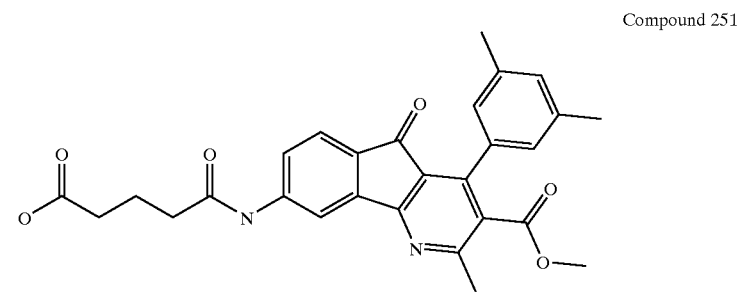

5H-indeno[1,2-b]pyridine-3-carboxylic acid, 8-[(4-carboxy-1-oxobutyl)amino]-4-(3,5-dimethylphenyl)-2-methyl-5-oxo-, methyl ester Compound 254

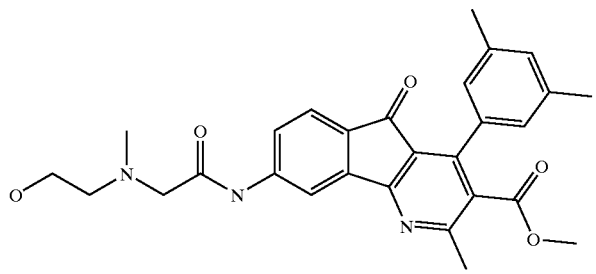

5H-indeno[1,2-b]pyridine-3-carboxylic acid, 4-(3,5-dimethylphenyl)-8-[[[(2-hydroxyethyl)methylamino]acetyl]amino]-2-methyl-5-oxo-, methyl ester Compound 261

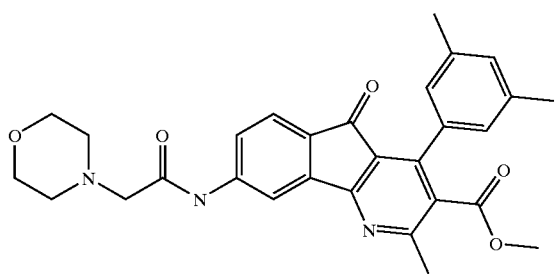

5H-indeno[1,2-b]pyridine-3-carboxylic acid, 4-(3,5-dimethylphenyl)-2-methyl-8-[(4-morpholinylacetyl)amino]-5-oxo-, methyl ester Compound 262

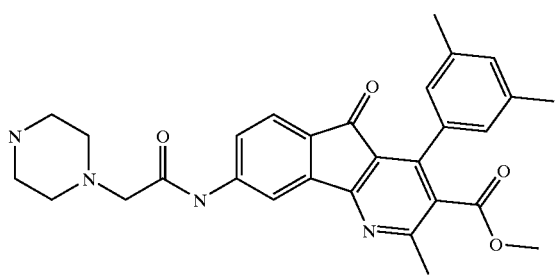

5H-indeno[1,2-b]pyridine-3-carboxylic acid, 4-(3,5-dimethylphenyl)-2-methyl-5-oxo-8-[(1-piperazinylacetyl)amino]-, methyl ester The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a pharmaceutical composition comprising the instant compound and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by reducing PDE activity in appropriate cells, which comprises administering to the subject a therapeutically effective dose of the instant pharmaceutical composition.

In one embodiment, the disorder is an inflammatory disorder. In another embodiment, the disorder is an AIDS-related disorder. Examples of disorders treatable by the instant pharmaceutical composition include, without limitation, organ transplantation, autoimmune disorders (e.g. arthritis), immune challenge such as a bee sting, inflammatory bowel disease, bronchial disorders (e.g. asthma), HIV/AIDS, cardiovascular disorder, erectile dysfunction, allergies, and psoriasis. In the preferred embodiment, the disorder is rheumatoid arthritis.

As used herein, the term "subject" includes, without limitation, any animal or artificially modified animal having a disorder ameliorated by reducing PDE activity in appropriate cells. In a preferred embodiment, the subject is a human. In a more preferred embodiment, the subject is a human.

As used herein, "appropriate cells" include, by way of example, cells which display PDE activity. Specific examples of appropriate cells include, without limitation, T-lymphocytes, muscle cells, neuro cells, adipose tissue cells, monocytes, macrophages, fibroblasts.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.001 mg/kg of body weight to about 200 mg/kg of body weight of the instant pharmaceutical composition. In another embodiment, the therapeutically and/or prophylactically effective dose is a dose sufficient to deliver from about 0.05 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0 µg/kg/min to about 10 mg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

This invention still further provides a method of preventing an inflammatory response in a subject, comprising administering to the subject a prophylactically effective amount of the instant pharmaceutical composition either preceding or subsequent to an event anticipated to cause the inflammatory response in the subject. In the preferred embodiment, the event is an insect sting or an animal bite.
Definitions and Nomenclature Unless otherwise noted, under standard nomenclature used throughout this disclosure the terminal portion of the designated side chain is described first, followed by the adjacent functionality toward the point of attachment.

As used herein, the following chemical terms shall have the meanings as set forth in the following paragraphs: "independently", when in reference to chemical substituents, shall mean that when more than one substituent exists, the substituents may be the same or different;.

"Alkyl" shall mean straight, cyclic and branched-chain alkyl. Unless otherwise stated, the alkyl group will contain 1–20 carbon atoms. Unless otherwise stated, the alkyl group may be optionally substituted with one or more groups such as halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, carboxamide, hydroxamic acid, sulfonamide, sulfonyl, thiol, aryl, aryl($c_1$–$c_8$)alkyl, heterocyclyl, and heteroaryl.

"Alkoxy" shall mean —O-alkyl and unless otherwise stated, it will have 1–8 carbon atoms.

"Halogen" shall mean fluorine, chlorine, bromine or iodine; "PH" or "Ph" shall mean phenyl; "Ac" shall mean acyl; "Bn" shall mean benzyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, 2-oxazepinyl, azepinyl, N-oxo-pyridyl, 1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, benzothiopyranyl, indazolyl, indolizinyl, benzofuryl, chromonyl, coumarinyl, cinnolinyl, quinoxalinyl, indazolyl, pyrrolopyridinyl, furopyridinyl (such as furo[2,3-c] pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, thienothienyl, and furyl. The heteroaryl group may be substituted by independent replacement of 1 to 5 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl) amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; and the like.

Substituted aryl, substituted heteroaryl, and substituted heterocycle may also be substituted with a second substituted-aryl, a second substituted-heteroaryl, or a second substituted-heterocycle to give, for example, a 4-pyrazol-1-yl-phenyl or 4-pyridin-2-yl-phenyl.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

I. General Synthetic Schemes

Representative compounds of the present invention can be synthesized in accordance with the general synthetic methods described below and illustrated in the following general schemes. The products of some schemes can be used as intermediates to produce more than one of the instant compounds. The choice of intermediates to be used to produce subsequent compounds of the present invention is a matter of discretion that is well within the capabilities of those skilled in the art.

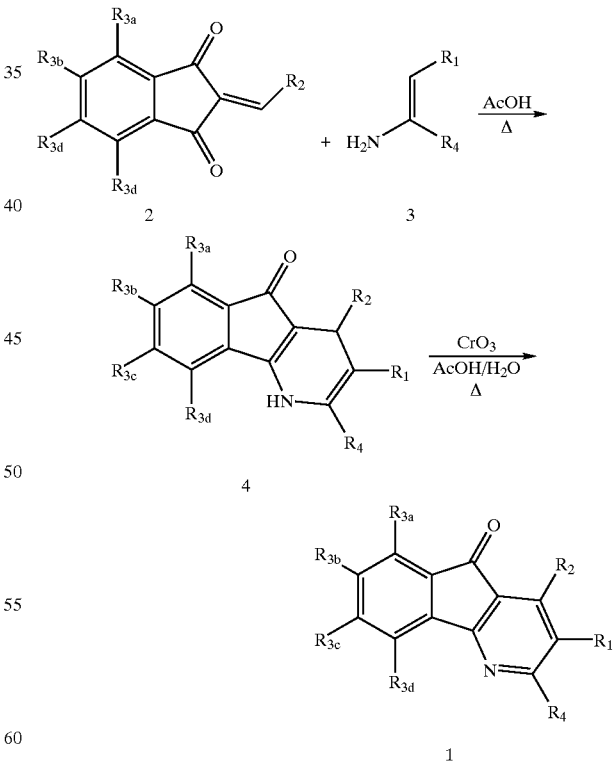

Procedures described in Scheme 1, wherein $R_{3a}$, $R_{3b}$, $R_{3c}$, and $R_{3d}$ are independently any $R_3$ group, and $R_1$, $R_2$, $R_3$, and $R_4$ are as described above, can be used to prepare compounds of the invention wherein X is O.

Benzylidenes 2 may be obtained by known methods (Bullington, J. L; Cameron, J. C.; Davis, J. E.; Dodd, J. H.; Harris, C. A.; Henry, J. R.; Pellegrino-Gensey, J. L.; Rupert, K. C.; Siekierka, J. J. Bioorg. Med. Chem. Lett. 1998, 8, 2489; Petrow, V.; Saper, J.; Sturgeon, B. J. Chem. Soc. 1949, 2134). Hantzsch reaction of the benzylidene compounds with enamines 3 can be performed in refluxing acetic acid (Petrow et al., supra). When the desired enamines are not available, alternate Hantzsch conditions may be utilized which involve adding ammonium acetate to the reaction. The resulting dihydropyridines 4 are oxidized with chromium trioxide to obtain the desired pyridines 1 (Petrow et al., supra). In cases where the substitution pattern on the fused aromatic ring ($R_3$) leads to a mixture of regioisomers, the products can be separated by column chromatography.

In some cases, especially where $R_2$ is an alkyl group, another modification of the Hantzsch may be performed which uses three components (Bocker, R. H.; Buengerich, P. J. Med. Chem. 1986, 29, 1596). Where $R_2$ is an alkyl group it is also necessary to perform the oxidation with DDQ or $MnO_2$ instead of chromium (VI) oxide (Vanden Eynde, J. J.; Delfosse, F.; Mayence, A.; Van Haverbeke, Y. Tetrahedron 1995, 51, 6511).

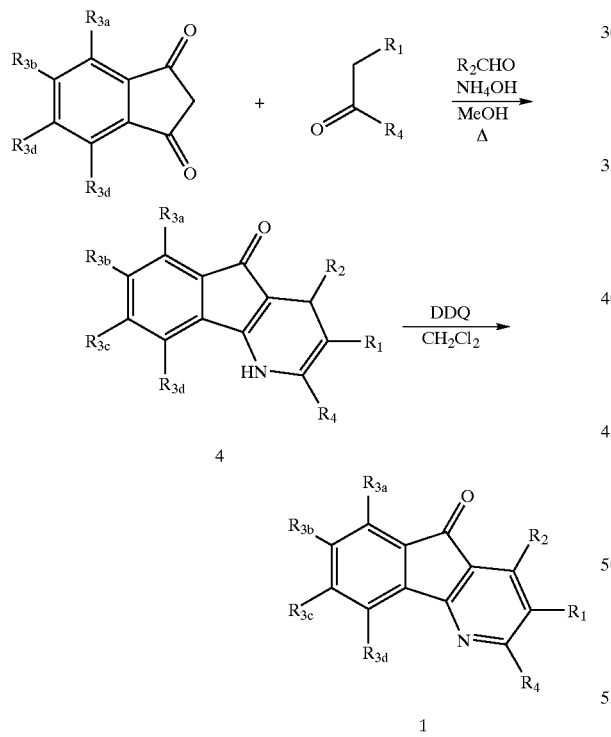

In order to obtain the corresponding carboxylic acids and amides, the cyanoethyl esters 5 are prepared as described above. The esters are converted to the carboxylic acids by treatment with sodium hydroxide in acetone and water (Ogawa, T.; Matsumoto, K.; Yokoo, C.; Hatayama, K.; Kitamura, K. J. Chem. Soc., Perkin Trans. 1 1993, 525). The corresponding amides can then be obtained from the acids using standard means.

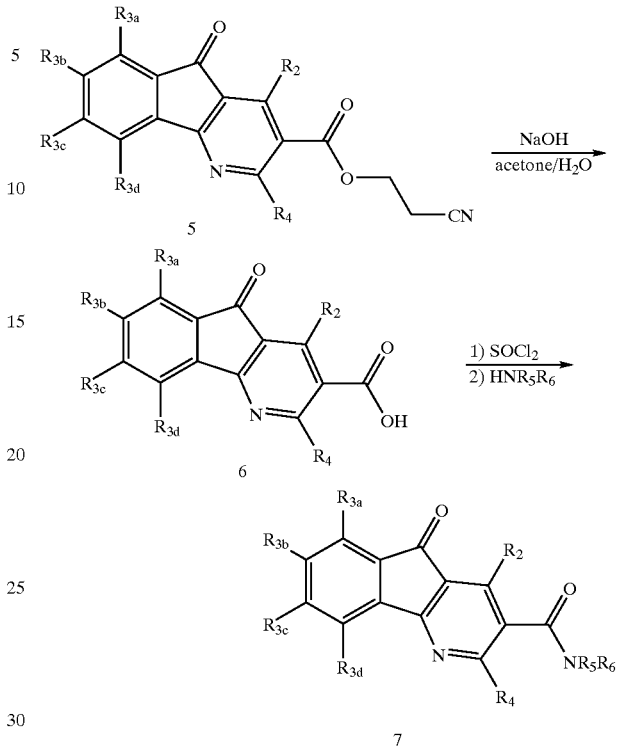

The procedure for making compounds where $R_4$ is $NH_2$ may be slightly modified. These compounds are prepared in one step from the benzylidenes 2 and alkyl amidinoacetate (Kobayashi, T.; Inoue, T.; Kita, Z.; Yoshiya, H.; Nishino, S.; Oizumi, K.; Kimura, T. Chem. Pharm. Bull. 1995, 43, 788) as depicted in Scheme 4 wherein R is $R_5$ or $R_6$ as described above.

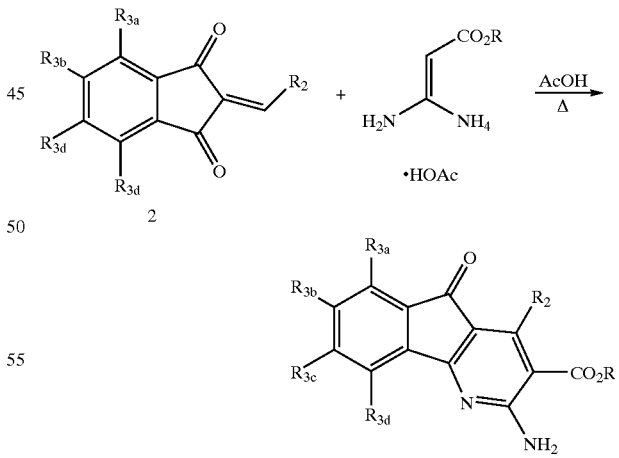

The dihydropyridine lactones 9 can be synthesized from benzylidenes 8 (Zimmer, H.; Hillstrom, W. W.; Schmidt, J. C.; Seemuth, P. D.; Vogeli, R. J. Org. Chem. 1978, 43, 1541) and 1,3-indanedione, as shown in Scheme 5, and the corresponding pyridine is then obtained by oxidation with manganese dioxide.

Scheme 5

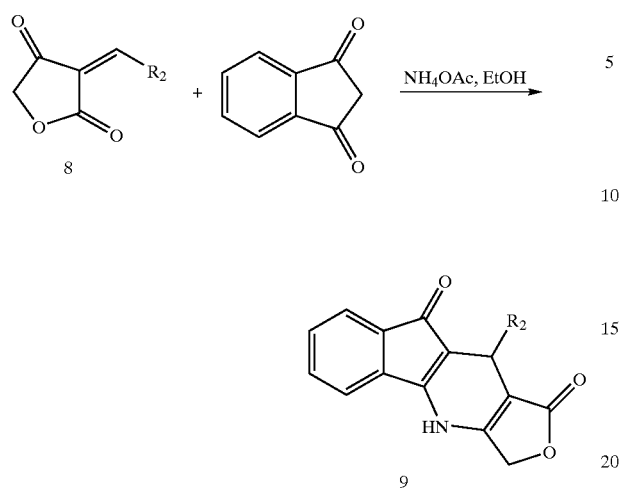

Representative schemes to modify substituents on the fused aromatic ring are shown below. The amines 11 are obtained from the corresponding nitro compounds 10 by reduction with tin (II) chloride (Scheme 6). Reaction of the amines with acetyl chloride provide the amides 12.

Scheme 6

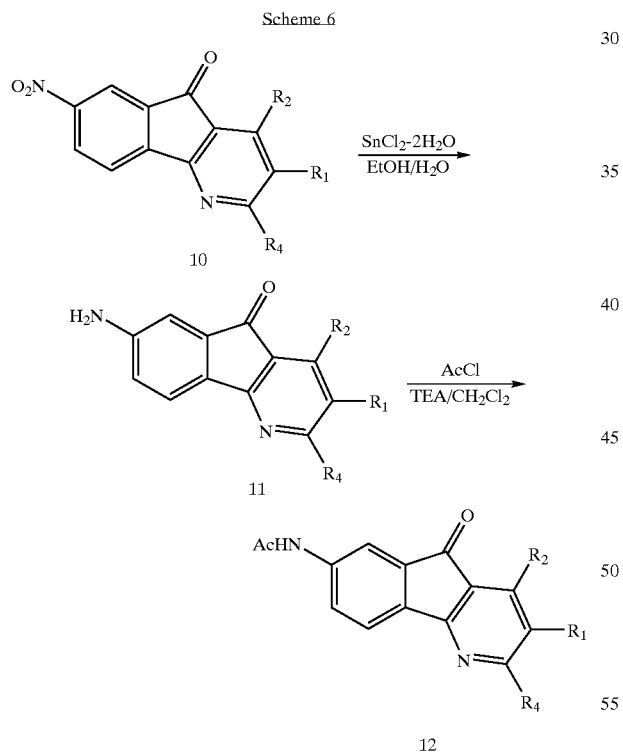

In accordance with Scheme 7 wherein Y is O, and n is an integer from 1–3, an alkyl chain with a carboxylic acid at the terminal end can also be added to the amines 11. For example, reaction with either succinic anhydride (Omuaru, V. O. T.; *Indian J. Chem.*, Sect B. 1998, 37, 814) or β-propiolactone (Bradley, G.; Clark, J.; Kernick, W. *J. Chem. Soc., Perkin Trans.* 1 1972, 2019) can provide the corresponding carboxylic acids 13. These carboxylic acids are then converted to the hydroxamic acids 14 by treatment with ethyl chloroformate and hydroxylamine (Reddy, A. S.; Kumar, M. S.; Reddy, G. R. *Tetrahedron Lett* 2000, 41, 6285).

Scheme 7

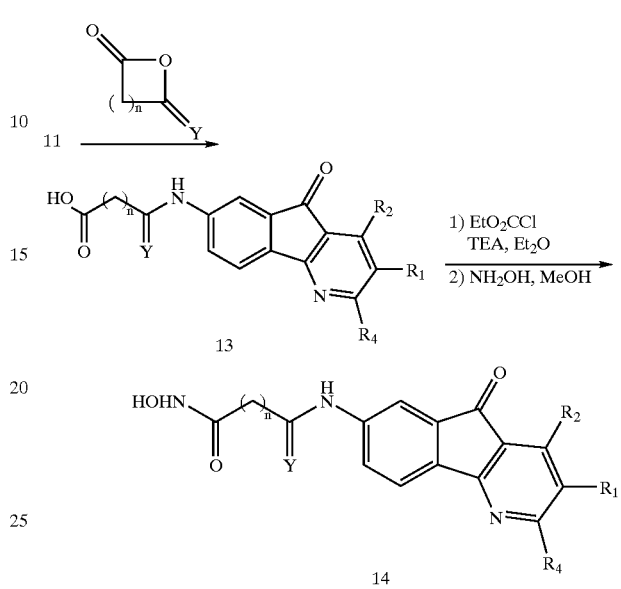

The amines 11 can also be treated with glycolic acid to afford alcohols 15 (Jursic, B. S.; Zdravkovski, Z. *Synthetic Comm.* 1993, 23, 2761) as shown in Scheme 8.

Scheme 8

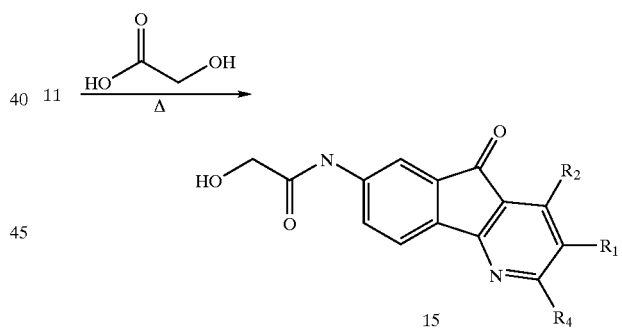

As shown in Scheme 9, the aminoindenopyridines 11 may also be treated with chloroacetylchloride followed by amines to provide the more elaborate amines 16 (Weissman, S. A.; Lewis, S.; Askin, D.; Volante, R. P.; Reider, P. J. *Tetrahedron Lett.* 1998, 39, 7459). Where $R_6$ is a hydroxyethyl group, the compounds can be further converted to piperazinones 17.

Scheme 9

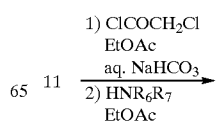

-continued

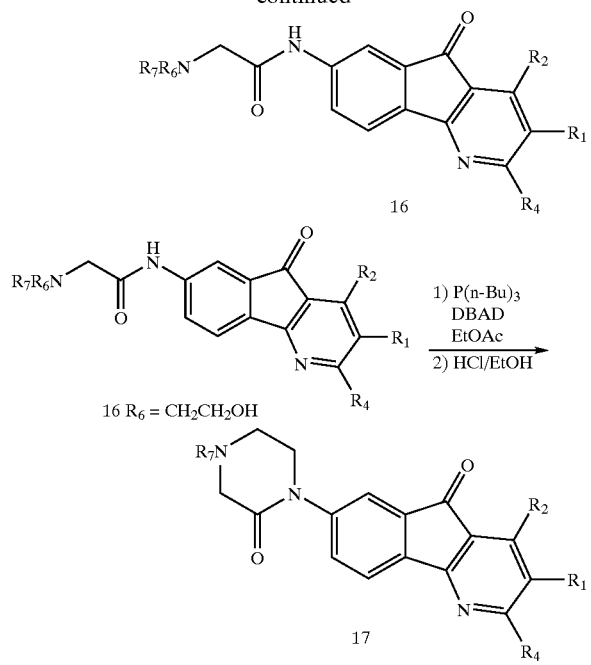

The 4-aminoindenopyridines 18 can be synthesized from the 4-chloroindenopyridines 19 using a known procedure (Gorlitzer, K.; Herbig, S.; Walter, R. D. *Pharmazie* 1997, 504) or via palladium catalyzed coupling (Scheme 10).

Scheme 10

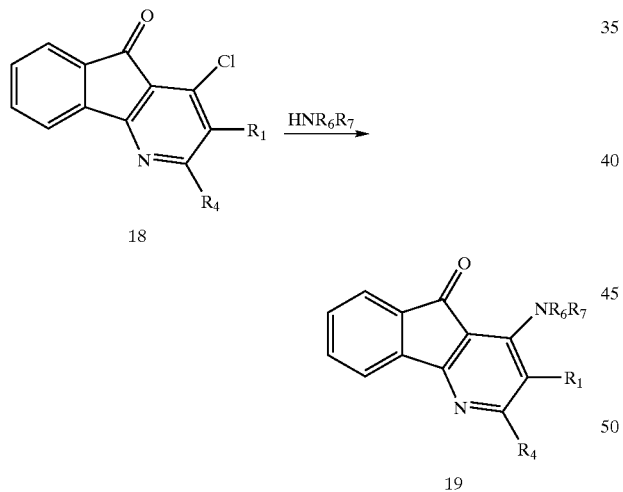

II. Specific Compound Syntheses

Specific compounds which are representative of this invention can be prepared as per the following examples. No attempt has been made to optimize the yields obtained in these reactions. Based on the following, however, one skilled in the art would know how to increase yields through routine variations in reaction times, temperatures, solvents and/or reagents.

The products of certain syntheses can be used as intermediates to produce more than one of the instant compounds. In those cases, the choice of intermediates to be used to produce compounds of the present invention is a matter of discretion that is well within the capabilities of those skilled in the art.

EXAMPLE 1

Hantzsch Condensation to Form Dihydropyridine 4

($R_1$=COOMe; $R_2$=3,5-dimethylphenyl; $R_{3b,c}$=Cl; $R_{3a,b}$=H; $R_4$=Me)

To a refluxing solution of benzylidene 2 (0.500 g, 1.5 mmol) in acetic acid (10 mL) was added methyl-3-aminocrotonate (0.695 g, 6.0 mmol). The reaction was heated to reflux for 20 minutes, then water was added until a precipitate started to form. The reaction was cooled to room temperature. The mixture was filtered and washed with water to obtain 0.354 g (55%) of a red solid. MS m/z 450 ($M^+$+23), 428 ($M^+$+1).

EXAMPLE 2

Alternate Hantzsch Conditions to Form Dihydropyridine 4

($R_1$=$CO_2$Me; $R_2$=2,4-dimethylphenyl; $R_3$=H; $R_4$=Et)

To a refluxing solution of benzylidene 2 (1.00 g, 3.82 mmol) in acetic acid (12 Ml) was added methyl propionylacetate (1.98 g, 15.2 mmol) and ammonium acetate (1.17 g, 15.2 mmol). The reaction was heated for 20 min and then cooled to room temperature. No product precipitated from the solution, so the reaction was heated to reflux and then water was added until a solid began to precipitate. After cooling to room temperature, the mixture was filtered and the red solid washed with water to yield 1.29 g (90%) of product. MS m/z 396 ($M^+$+23), 374 ($M^+$+1).

EXAMPLE 3

Oxidation of Dihydropyridine 4 to Pyridine 1

($R_1$=COOMe, $R_2$=3,5-dimethylphenyl; $R_{3b,c}$=Cl; $R_{3a,d}$=H; $R_4$=Me)

To a refluxing solution of dihydropyridine 4 (0.250 g, 0.58 mmol) in acetic acid (10 mL) was added a solution of chromium (VI) oxide (0.584 g, 0.58 mmol) in 1 mL water. After 30 minutes at reflux, the reaction was diluted with water until a precipitate started to form. The mixture was cooled to room temperature and allowed to stand overnight. The mixture was filtered and washed with water to give 0.199 g (81%) of a yellow solid. MS m/z 448 ($M^+$+23), 426 ($M^+$+1).

EXAMPLE 4

Oxidation of Dihydropyridine 4 to Pyridine 1

($R_1$=COOMe; $R_2$=(4-methyl)-1-naphthyl; $R_{3b,c}$=H, $NO_2$/$NO_2$, H; R=Me)

To a refluxing suspension of regioisomeric dihydropyridines 4 (3.59 g, 8.16 mmol) in acetic acid (40 mL) was added a solution of chromium (VI) oxide (0.816 g, 8.16 mmol) in 3 mL water. After 20 minutes at reflux, the reaction was diluted with water until a precipitate started to form. The mixture was cooled to room temperature and allowed to stand overnight. The mixture was filtered and washed with water to yield the mixture of regioisomers as a yellow solid. The products were purified by column chromatography eluting with hexanes:ethyl acetate to yield 1.303 g (37%) of pyridine 1 ($R_{3b}$=$NO_2$; $R_{3c}$=H) and 0.765 g (21%) of its regioisomer ($R_{3b}$=H: $R_{3c}$=$NO_2$). MS m/z 461 ($M^+$+23), 439 ($M^+$+1).

EXAMPLE 5

Alternate Three Component Hantzsch Reaction to Form Dihydropyridine 4

($R_1$=$CO_2$Me; $R_2$=cyclohexyl; $R_3$=H; $R_4$=Me)

Cyclohexane carboxaldehyde (2.0 g, 17.8 mmol), 1,3-indandione (2.6 g, 17.8 mmol), methylacetoacetate (2.0 g, 17.8 mmol), and ammonium hydroxide (1 mL) were refluxed in 8 mL of methanol for 1.5 hours. The temperature was lowered to approximately 50° C. and the reaction was stirred overnight. The reaction was cooled to room temperature, filtered and the solid washed with water. The residue was then dissolved in hot ethanol and filtered while hot. The filtrate was concentrated to yield 4.1 g (68%) of the product which was used without purification. MS m/z 336 ($M^-$−1).

EXAMPLE 6

DDQ Oxidation of Dihydropyridine 4

($R_1$=$CO_2$Me; $R_2$=cyclohexyl; $R_3$=H; $R_4$=Me)

To a solution of dihydropyridine 4 (2.50 g, 7.40 mmol) in 15 mL of dichloromethane was added 2,3-dichloro-3,6-dicyano-1,4-benzoquinone (1.70 g, 7.40 mmol). The reaction was stirred at room temperature for four hours. The mixture was filtered and the residue was washed with dichloromethane. After the filtrate was concentrated, the residue was purified by column chromatography eluting with ethyl acetate: hexanes to yield 0.565 g (23%) of a yellow solid. MS m/z 358 ($M^+$+23), 336 ($M^+$+1).

EXAMPLE 7

$MnO_2$ Oxidation of Dihydropyridine 4

($R_1$=$CO_2$Me; $R_2$=4-(dimethylamino)phenyl; $R_3$=H; $R_4$=Me)

To a solution of dihydropyridine 4 (0.50 g, 1.3 mmol) in 10 mL of dichloromethane was added manganese dioxide (2.5 g, 28.7 mmol). The reaction was stirred at room temperature overnight before filtering and washing with dichloromethane. The filtrate was concentrated to yield 0.43 g (88%) of orange solid 1. MS m/z 395 ($M^+$+23), 373 ($M^+$+1).

EXAMPLE 8

Cleavage of Carboxylic Ester 5

($R_2$=2,4-dimethylphenyl; $R_3$=H; $R_4$=Me)

To a suspension of ester 5 (2.75 g, 6.94 mmol) in acetone (50 mL) was added aqueous 1 M NaOH (100 mL). After stirring at room temperature for 24 hours, the reaction mixture was diluted with 100 mL of water and washed with dichloromethane (2×100 mL). The aqueous layer was cooled to 0° C. and acidified with concentrated HCl. The mixture was filtered and washed with water to yield 1.84 g (77%) yellow solid 6. MS m/z 366 ($M^+$+23), 343 ($M^+$+1).

EXAMPLE 9

Preparation of Amide 7

($R_2$=2,4-dimethylphenyl; $R_3$=H; $R_4$=Me; $R_5$=H; $R_6$=Me)

A solution of carboxylic acid 6 (0.337 g, 0.98 mmol) in thionyl chloride (10 mL) was heated at reflux for 1 hour. The solution was cooled and concentrated in vacuo. The residue was diluted with $CCl_4$ and concentrated to remove the residual thionyl chloride. The residue was then dissolved in THF (3.5 mL) and added to a 0° C. solution of methylamine (1.47 mL of 2.0 M solution in THF, 2.94 mmol) in 6.5 mL THF. The reaction was warmed to room temperature and stirred overnight. The mixture was poured into water, filtered, washed with water and dried to yield 0.263 g (75%) of tan solid. MS m/z 357 ($M^+$+1).

EXAMPLE 10

Preparation of Pyridine 1

($R_1$=$CO_2$Et; $R_2$=4-nitrophenyl; $R_3$=H; $R_4$=$NH_2$)

To a refluxing solution of benzylidene 2 (1.05 g, 3.76 mmol) in 10 mL of acetic acid was added ethyl amidinoacetate acetic acid salt (0.720 g, 3.76 mmol). The resulting solution was heated at reflux overnight. After cooling to room temperature, the resulting precipitate was removed by filtration and washed with water. This impure residue was heated in a minimal amount of ethanol and then filtered to yield 0.527 g (35%) of a yellow solid. MS m/z 412 ($M^+$+23), 390 ($M^+$+1).

EXAMPLE 11

Hantzsch Condensation of Benzylidene 8

($R_2$=3-methoxyphenyl) and 1,3-indandione)

The benzylidene 8 (2.00 g, 9.2 mmol), 1,3-indandione (1.34 g, 0.2 mmmol) and ammonium acetate (2.83 g, 36.7 mmol) were added to 30 mL of ethanol and heated to reflux overnight. The reaction mixture was cooled to room temperature and diluted with ethanol. A yellow precipitate was collected by filtration, washed with ethanol, and dried under vacuum to yield 1.98 g (63%) of the dihydropyridine 9. MS m/z 346 ($M^+$+1).

EXAMPLE 12

Reduction to Prepare Amine 11

($R_1$=$CO_2$Me; $R_2$=4-methylnaphthyl; $R_4$=Me)

To a refluxing suspension of pyridine 10 (0.862 g, 1.97 mmol) in 35 mL of ethanol was added a solution of tin (II) chloride dihydrate (1.33 g, 5.90 mmol) in 6 mL of 1:1 ethanol: concentrated HCl. The resulting solution was heated at reflux overnight. Water was added until a precipitate started to form and the reaction was cooled to room temperature. The mixture was then filtered and washed with water. After drying, the residue was purified by column chromatography eluting with hexanes: ethyl acetate to yield 0.551 g (69%) of an orange solid. MS m/z 431 ($M^+$+23), 409 ($M^+$+1).

EXAMPLE 13

Acetylation of Amine 11

($R_1$=$CO_2$Et; $R_2$=3,4-methylenedioxyphenyl; $R_4$=Me)

To a solution of amine 11 (0.070 g, 0.174 mmol) in 15 mL of dichloromethane was added triethylamine (0.026 g, 0.261 mmol) and acetyl chloride (0.015 g, 0.192 mmol). After stirring overnight at room temperature, the reaction mixture was diluted with water and then extracted with dichloromethane (3×35 mL). The combined organics were washed with brine, dried over $MgSO_4$, and concentrated. The residue was purified by silica gel chromatography eluting with hexanes: ethyl acetate to yield 0.054 g (70%) of amide 12. MS m/z 467 ($M^+$+23), 445 ($M^+$+1).

EXAMPLE 14

Preparation of Carboxylic Acid 13

($R_1$=$CO_2Me$; $R_2$=3,5-dimethylphenyl; $R_4$=Me; Y=O; n=2)

To a suspension of amine 11 (0.079 g, 0.212 mmol) in 5 mL of benzene was added succinic anhydride (0.021 g, 0.212 mmol). After heating at reflux for 24 hours, the reaction mixture was filtered and washed with benzene. The residue was dried under high vacuum and then washed with ether to remove the excess succinic anhydride. This yielded 0.063 g (63%) of carboxylic acid 13. MS m/z 473 ($M^+$+1).

EXAMPLE 15

Preparation of Carboxylic Acid 13

($R_1$=$CO_2Me$; $R_2$=3,5-dimethylphenyl; $R_4$=Me; Y=$H_2$; n=1)

To a refluxing solution of amine 11 (0.078 g, 0.210 mmol) in 5 mL of acetonitrile was added β-propiolactone (0.015 g, 0.210 mmol). The reaction was heated to reflux for 72 hours before cooling to room temperature. The reaction mixture was concentrated. The residue was mixed with 10% aqueous sodium hydroxide and washed sequentially with ether and ethyl acetate. The aqueous layer was acidified with concentrated HCl and extracted with dichloromethane (2×25 mL). The combined organics were dried over $MgSO_4$, filtered, and concentrated. The residue was purified by column chromatography eluting with 5% MeOH in dichloromethane to yield 0.020 g (21%) of an orange solid. MS m/z 467 ($M^+$+23), 445 ($M^+$+1).

EXAMPLE 16

Preparation of Hydroxamic Acid 14

($R_1$=$CO_2Me$; $R_2$=(4-methyl)-1-naphthyl; Y=O; n=2; $R_4$=Me)

To a 0° C. suspension of carboxylic acid 13 (0.054 g, 0.106 mmol) in 10 mL of diethyl ether was added triethylamine (0.014 g, 0.138 mmol) and then ethyl chloroformate (0.014 g, 0.127 mmol). The mixture was stirred at 0° C. for 30 minutes and them warmed to room temperature. A solution of hydroxylamine (0.159 mmol) in methanol was added and the reaction was stirred overnight at room temperature. The mixture was filtered and the residue was washed with ether and dried under vacuum to yield 0.030 g (54%) of a yellow solid. MS m/z 524 ($M^+$+1).

EXAMPLE 17

Preparation of Amide 15

($R_1$=$CO_2Me$; $R_2$=3,5-dimethylphenyl; $R_4$=Me)

A mixture of amine 11 (0.201 g, 0.54 mmol) and glycolic acid (0.049 g, 0.65 mmol) was heated at 120–160° C. for 30 minutes. During heating, more glycolic acid was added to ensure that excess reagent was present. Once the starting material was consumed, the reaction was cooled to room temperature, and diluted with dichloromethane. The resulting mixture was extracted with 20% NaOH, followed by 10% HCl, and finally water. The combined organics were concentrated and triturated with ether. Purification by column chromatography eluting with ethyl acetate: hexanes yielded 0.012 g (5%) of a yellow solid. MS m/z 453 ($M^+$+23), 431 ($M^+$+1).

EXAMPLE 18

Preparation of Amide 16

($R_1$=$CO_2Me$; $R_2$=3,5-dimethylphenyl; $R_4$=Me; $NR_6R_7$=morpholino)

To a 0° C. mixture of amine 11 (0.123 g, 0.331 mmol) in 2 mL of 20% aqueous $NaHCO_3$ and 3 mL of ethyl acetate was added chloroacetyl chloride (0.047 g, 0.413 mmol). The reaction was warmed to room temperature and stirred for 45 minutes. The mixture was poured into a separatory funnel and the aqueous layer was removed. The organic layer containing the crude chloroamide was used without purification. To the ethyl acetate solution was added morpholine (0.086 g, 0.992 mmol) and the reaction was heated to approx. 65° C. overnight. The reaction was diluted with water and cooled to room temperature. After extraction with ethyl acetate (3×25 mL), the combined organics were washed with brine, dried over $MgSO_4$ and concentrated to yield 0.130 g (79%) of a yellow solid. MS m/z 522 ($M^+$+23), 500 ($M^+$+1).

EXAMPLE 19

Preparation of Piperazinone 17

($R_1$=$CO_2Me$; $R_2$=3,5-dimethylphenyl; $R_4$=Me; $R_7$=H)

To a 0° C. solution of amide 16 ($R_6$=$CH_2CH_2OH$) (0.093 g, 0.20 mmol), tri n-butylphosphine (0.055 g, 0.27 mmol) in 0.35 mL ethyl acetate was slowly added di-tert-butyl azodicarboxylate (0.062 g, 0.27 mmol) in 0.20 mL ethyl acetate. The reaction was allowed to stand for 15 minutes and then heated to 40° C. overnight. 4.2 M ethanolic HCl was added dropwise. The mixture was cooled to 0° C. and allowed to stand for 2 hours. The mixture was filtered and washed with cold ethyl acetate. Purification by column chromatography with 1–5% MeOH in $CH_2Cl_2$ yielded 0.011 (12%) of a white solid. MS m/z 478 ($M^+$+23), 456 ($M^+$+1).

EXAMPLE 20

Preparation of 4-Aminoindenopyridine 19

($R_1$=$CO_2Me$; $R_4$=Me; $R_6$=Me; $R_7$=phenyl)

To a solution of 4-chloroindenopyridine 18 (0.069 g, 0.240 mmol) in 10 mL of 2-ethoxyethanol was added N-methylaniline (0.026 g, 0.240 mmol). The reaction was heated at reflux for 96 hours. After cooling to room temperature, the solution was concentrated. The residue was purified by column chromatography eluting with hexanes: ethyl acetate to yield 0.029 g (34%) of an orange solid. MS m/z 359 ($M^+$+1).

EXAMPLE 21

Preparation of 4-Aminoindenopyridine 19

($R_1$=$CO_2Me$; $R_4$=Me; $R_6$=H; $R_7$=cyclopentyl) by Palladium Catalyzed Coupling A mixture of 4-chloroindenopyridine 18 (0.100 g, 0.347 mmol), cyclopentylamine (0.035 g, 0.416 mmol), palladium (II) acetate (0.004 g, 0.0017 mmol), 2-(di-t-butylphosphino) biphenyl (0.010 g, 0.0035 mmol), and cesium carbonate (0.124 g, 0.382 mmol) in 10 mL of dioxane was heated at reflux overnight. The reaction was cooled to room temperature, diluted with water, and extracted with ethyl acetate (3×35 mL). The combined organics were washed with brine, dried over $Na_2SO_4$, and concentrated. The residue was purified by column chromatography eluting with ethyl acetate: hexanes. The purified oil was dissolved in ether and cooled to 0° C. To this solution was slowly added 1.0 M HCl in ether. The resulting precipitate was isolated by filtration, washed with ether, and dried under vacuum to yield 0.032 g (25%) of a yellow solid. MS m/z 359 ($M^+$+23), 337 ($M^+$+1).

Following the general synthetic procedures outlined above and in Examples 1–21, the compounds of Table 1 below were prepared.

TABLE 1
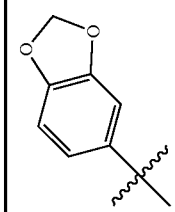
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 1 | CN | C$_7$H$_5$O$_2$ | H | H | H | H | Me | 341 |
| 2 | CO$_2$Et | C$_7$H$_5$O$_2$ | H | H | H | H | Me | 388 |
| 3 | CO$_2$t-Bu | C$_7$H$_5$O$_2$ | H | H | H | H | Me | 416 |

TABLE 1-continued

[Structure Ia: tricyclic indeno-pyridinone with R1, R2 on pyridine ring (R4 adjacent to N), and R3a, R3b, R3c, R3d on the benzo ring; C=O at the 5-membered ring junction]

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 4 | CO$_2$t-Bu | 3,4-dimethoxyphenyl (C$_8$H$_9$O$_2$) | H | H | H | H | Me | 432 |
| 5 | CO$_2$Et | 4-nitrophenyl (C$_6$H$_4$NO$_2$) | H | H | H | H | Me | 389 |
| 6 | CO$_2$H | 3,4-methylenedioxyphenyl (C$_7$H$_5$O$_2$) | H | H | H | H | Me | 360 |

TABLE 1-continued
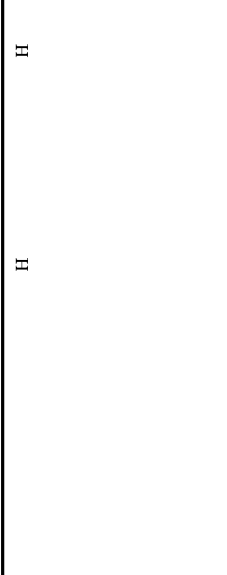
| No. | R₁ | R₂ | R₃ₐ | R₃ᵦ | R₃꜀ | R₃d | R₄ | MS (M + 1) |
|---|---|---|---|---|---|---|---|---|
| 7 | CO₂Et | 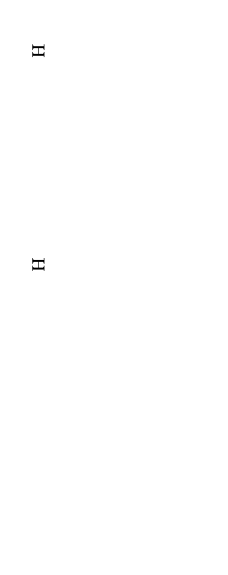 C₁₄H₁₃O₂ | H | H | H | H | Me | 480 |
| 8 | CO₂Et |  C₈H₈BrO₂ | H | H | H | H | Me | 482 |
| 9 | CO₂Et |  C₁₁H₉O | H | H | H | H | Me | 424 |

TABLE 1-continued
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 10 | $CO_2H$ |  $C_8H_9O_2$ | H | H | H | H | Me | 376 |
| 11 | $CO_2Et$ | Ph | | | | | | |
| 12 | $CO_2Et$ |  $C_7H_7O$ | H | H | H | H | Me | 344 |
| | | | | | | | Me | 374 |
| 13 | $CO_2Et$ |  $C_9H_{11}O_3$ | H | H | H | H | Me | 434 |

TABLE 1-continued
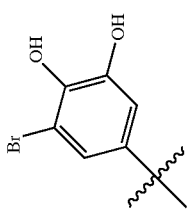
Ia
| No. | R₁ | R₂ | R₃ₐ | R₃ᵦ | R₃c | R₃d | R₄ | MS (M + 1) |
|---|---|---|---|---|---|---|---|---|
| 14 | CO₂Et | 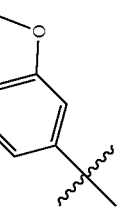 C₆H₄BrO₂ | H | H | H | H | Me | 454 |
| 15 | CO₂Bn | 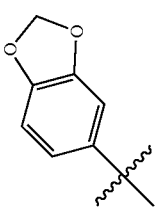 C₇H₅O₂ | H | H | H | H | Me | 450 |
| 16 |  C₁₁H₁₄NO₂ | C₇H₅O₂ | H | H | H | H | Me | 507 |

TABLE 1-continued
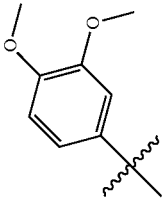
Ia
| No. | R₁ | R₂ | R₃ₐ | R₃ᵦ | R₃꜀ | R₃d | R₄ | MS (M + 1) |
|---|---|---|---|---|---|---|---|---|
| 17 | CO₂Me | 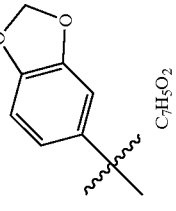 C₈H₉O₂ | H | H | H | H | Me | 390 |
| 18 | CO₂Me | 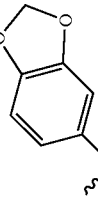 C₇H₅O₂ | H | H | H | H | Me | 374 |
| 19 | CO₂Et | 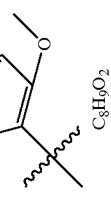 C₈H₉O₂ | H | H | H | H | Me | 404 |

TABLE 1-continued

Structure Ia: tetracyclic ketone with substituents R1, R2, R3a, R3b, R3c, R3d, R4 on the fused ring system containing pyridine nitrogen.

| No. | R1 | R2 | R3a | R3b | R3c | R3d | R4 | MS (M+1) |
|---|---|---|---|---|---|---|---|---|
| 20 | CO2Et | 2,4-dimethoxyphenyl, C8H9O2 | H | H | H | H | Me | 404 |
| 21 | CO2Et | 5-bromo-2-methoxyphenyl, C7H6BrO | H | H | H | H | Me | 454 |
| 22 | CO2Et | benzo[1,3]dioxol-5-yl, C7H5O2 | H | H | H | H | NH2 | 411 (M+23) |

TABLE 1-continued
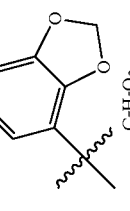
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 23 | $CO_2Et$ | 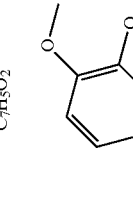 $C_7H_5O_2$ | H | H | H | H | Me | 388 |
| 25 | $CO_2Et$ | 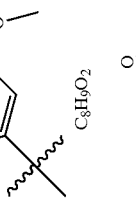 $C_8H_9O_2$ | H | H | H | H | $NH_2$ | 405 |
| 26 | $CO_2Et$ | 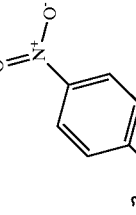 $C_6H_4NO_2$ | H | H | H | H | $NH_2$ | 390 |
| 27 | $CO_2Et$ | Ph | H | H | H | H | $NH_2$ | 345 |

TABLE 1-continued
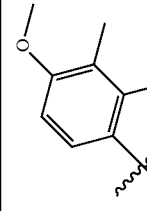
| No. | R₁ | R₂ | R₃ₐ | R₃ᵦ | R₃c | R₃d | R₄ | MS (M + 1) |
|---|---|---|---|---|---|---|---|---|
| 28 | CO₂Et | 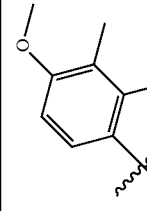 C₉H₁₁O | H | H | H | H | Me | 402 |
| 29 | CO₂Et | 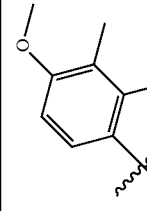 C₈H₈BrO₂ | H | H | H | H | Me | 483 |
| 30 | CO₂Me | Ph | H | H | H | H | Me | 330 |
| 31 | CO₂Et | 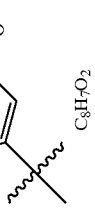 C₈H₇O₂ | H | H | H | H | Me | 402 |

TABLE 1-continued
| No. | R₁ | R₂ | R₃ₐ | R₃ᵦ | R₃c | R₃d | R₄ | MS (M+1) |
|---|---|---|---|---|---|---|---|---|
| 32 | CO₂Et | 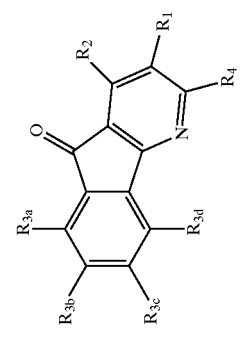 C₇H₅O₂ | H | NO₂ | H | H | Me | 433 |
| 33 | 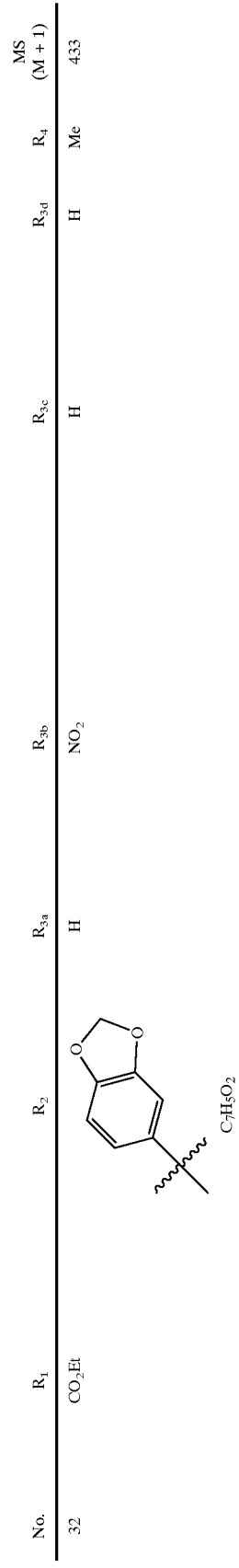 C₄H₄NO₂ | 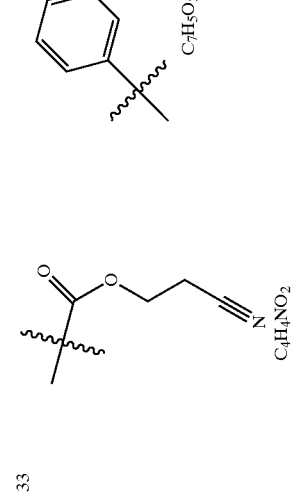 C₇H₅O₂ | H | H | H | H | Me | 413 |
| 34 | CO₂Et | 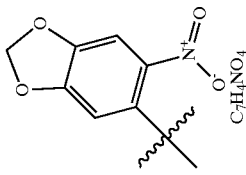 C₇H₄NO₄ | H | H | H | H | Me | 433 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 35 | CO₂Et | 1,3-benzodioxol-5-yl, C₇H₅O₂ | H | H | NO₂ | H | Me | 433 |
| 36 | CO₂Me | 3-(trifluoromethyl)phenyl, C₇H₄F₃ | H | H | H | H | Me | 398 |
| 37 | CO₂Et | 1,3-benzodioxol-5-yl, C₇H₅O₂ | H | H | NH₂ | H | Me | 403 |

TABLE 1-continued
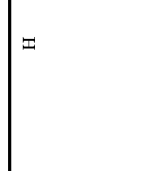
Ia
| No. | R₁ | R₂ | R₃ₐ | R₃ᵦ | R₃꜀ | R₃d | R₄ | MS (M + 1) |
|---|---|---|---|---|---|---|---|---|
| 38 | CONH₂ |  C₇H₅O₂ | H | H | H | H | Me | 359 |
| 39 | CO₂Et |  C₈H₉ | H | H | H | H | Me | 372 |
| 40 | CO₂Et |  C₇H₅O₂ | H | NH₂ | H | H | Me | 403 |

TABLE 1-continued
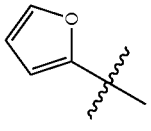
| No. | R₁ | R₂ | R₃ₐ | R₃ᵦ | R₃c | R₃d | R₄ | MS (M + 1) |
|---|---|---|---|---|---|---|---|---|
| 41 | CO₂Et |  C₄H₃O | H | H | H | H | Me | 334 |
| 42 | CO₂Et | 2-Thienyl | H | H | H | H | Me | 350 |
| 43 | CO₂Me | 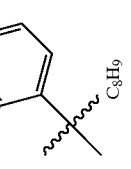 C₈H₉ | H | H | H | H | Me | 358 |
| 44 | CO₂Me | 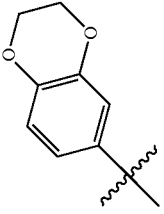 C₈H₇O₂ | H | H | H | H | Me | 388 |

TABLE 1-continued
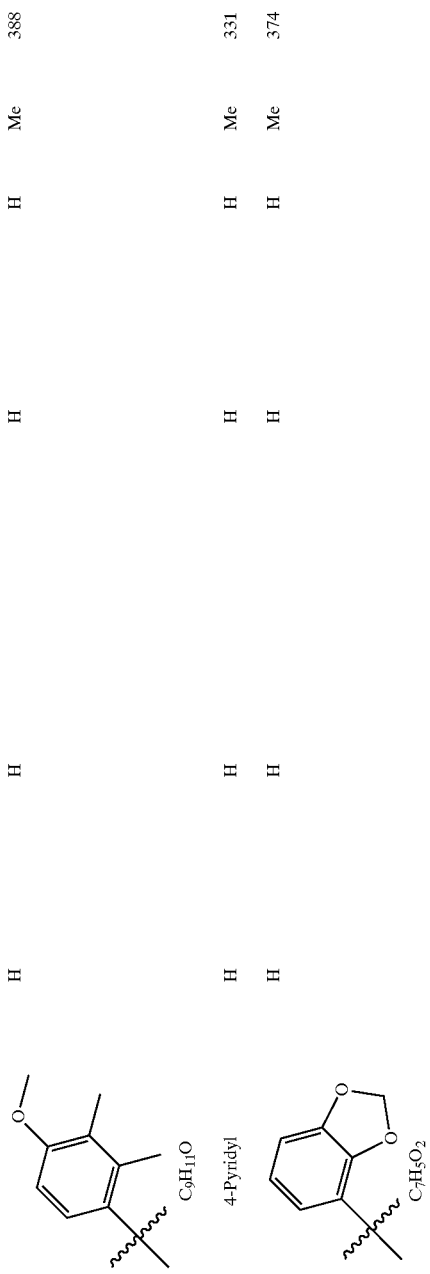
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 45 | $CO_2Me$ | 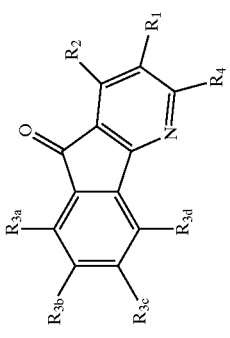 $C_7H_4NO_4$ | H | H | H | H | Me | 419 |
| 46 | $CO_2Me$ | 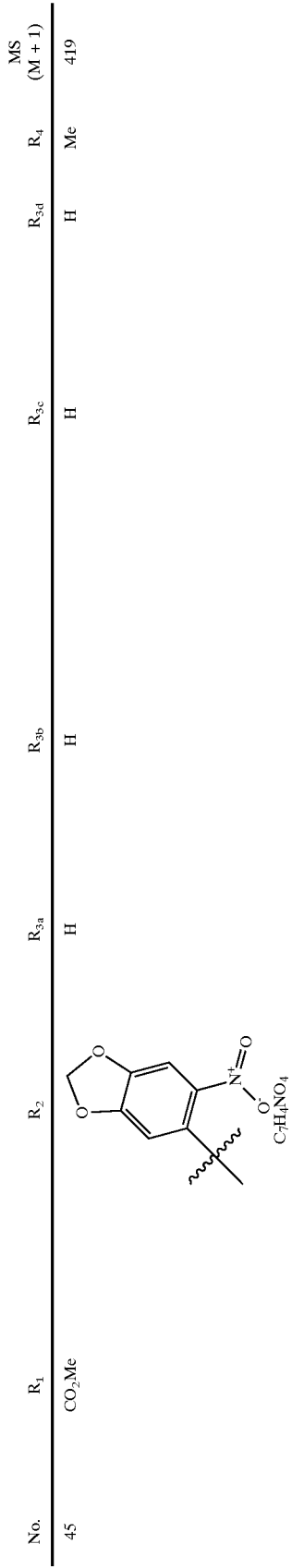 $C_9H_{11}O$ | H | H | H | H | Me | 388 |
| 47 | $CO_2Me$ | 4-Pyridyl | H | H | H | H | Me | 331 |
| 48 | $CO_2Me$ | $C_7H_5O_2$ | H | H | H | H | Me | 374 |

TABLE 1-continued
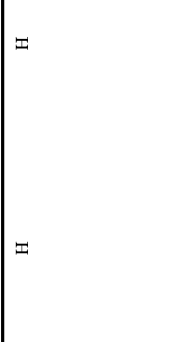
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 49 | CO$_2$Me |  6-bromo-benzo[1,3]dioxol-5-yl, C$_7$H$_4$BrO$_2$ | H | H | H | H | Me | 454 |
| 50 | CO$_2$Me | 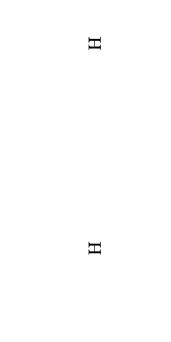 4-bromo-2-methoxyphenyl, C$_7$H$_6$BrO | H | H | H | H | Me | 439 |
| 51 | CO$_2$Me | 3,5-dimethylphenyl, C$_8$H$_9$ | H | H | H | H | Me | 358 |

TABLE 1-continued
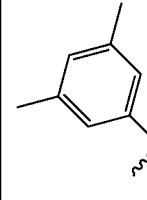
| No. | R₁ | R₂ | R₃ₐ | R₃ᵦ | R₃c | R₃d | R₄ | MS (M + 1) |
|---|---|---|---|---|---|---|---|---|
| 52 | CO₂Et |  3,5-dimethylphenyl, C₈H₉ | H | H | H | H | Me | 372 |
| 53 | CO₂Me | 4-methoxynaphthyl, C₁₁H₉O | H | H | H | H | Me | 410 |
| 54 | CO₂Me | 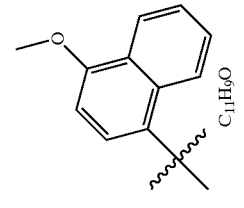 4-nitrophenyl, C₆H₄NO₂ | H | H | H | H | Me | 375 |

TABLE 1-continued
Ia
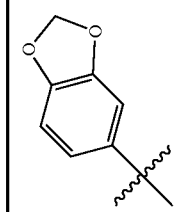
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 55 | $CO_2Et$ | 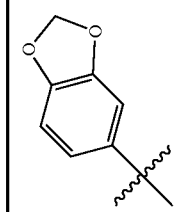 benzo[1,3]dioxol-5-yl, $C_7H_5O_2$ | H | NHAc | H | H | Me | 445 |
| 56 | $CO_2Et$ | benzo[1,3]dioxol-5-yl, $C_7H_5O_2$ | H | H | NHAc | H | Me | 445 |
| 57 | $CO_2Et$ | 3-methylphenyl, $C_7H_7$ | H | H | H | H | Me | 358 |
| 58 | $CO_2Et$ | 2-methylphenyl, $C_7H_7$ | H | H | H | H | Me | 358 |

TABLE 1-continued

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 59 | CO$_2$Et | 4-methylphenyl-C(CH$_3$)-, C$_7$H$_7$ | H | H | H | H | Me | 358 |
| 60 | CO$_2$Et | 3-(trifluoromethyl)phenyl-C(CH$_3$)-, C$_7$H$_4$F$_3$ | H | NO$_2$ | H | H | Me | 457 |
| 61 | CO$_2$Et | 3-(trifluoromethyl)phenyl-C(CH$_3$)-, C$_7$H$_4$F$_3$ | H | H | NO$_2$ | H | Me | 457 |
| 62 | CO$_2$Me | 2-methylphenyl-C(CH$_3$)-, C$_7$H$_7$ | H | H | H | H | Me | 344 |

TABLE 1-continued

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 63 | $CO_2Et$ | 3-(trifluoromethyl)phenyl, $C_7H_4F_3$ | H | $NH_2$ | H | H | Me | 427 |
| 64 | $CO_2Et$ | 3-(trifluoromethyl)phenyl, $C_7H_4F_3$ | H | H | $NH_2$ | H | Me | 427 |
| 65 | $CO_2Me$ | 3,5-bis(trifluoromethyl)phenyl, $C_8H_3F_6$ | H | H | H | H | Me | 466 |

TABLE 1-continued
| No. | R₁ | R₂ | R₃ₐ | R₃ᵦ | R₃c | R₃d | R₄ | MS (M+1) |
|---|---|---|---|---|---|---|---|---|
| 66 | CO₂Me | 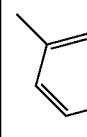 4-methylphenyl, C₇H₇ | H | H | H | H | Me | 344 |
| 67 | CO₂Me | 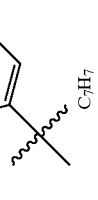 3-methylphenyl, C₇H₇ | H | H | H | H | Me | 344 |
| 68 | CO₂Me | 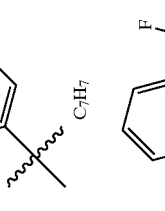 3-(trifluoromethyl)phenyl, C₇H₄F₃ | H | NO₂ | H | H | Me | 443 |
| 69 | CO₂Me | 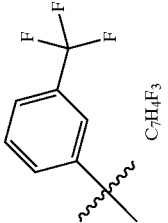 3-(trifluoromethyl)phenyl, C₇H₄F₃ | H | H | NO₂ | H | Me | 443 |

TABLE 1-continued

Ia (structure shown with R1, R2, R3a, R3b, R3c, R3d, R4 substituents on the indeno-pyridinone core)

| No. | R1 | R2 | R3a | R3b | R3c | R3d | R4 | MS (M + 1) |
|---|---|---|---|---|---|---|---|---|
| 70 | $CO_2Et$ | 2,4-dimethylphenyl-C(Me)- ($C_8H_9$) | H | H | H | H | i-Pr | 400 |
| 71 | $CO_2Me$ | 3-(trifluoromethyl)phenyl-C(Me)- ($C_7H_4F_3$) | H | $NH_2$ | H | H | Me | 413 |
| 72 | $CO_2Me$ | 3,5-dichlorophenyl-C(Me)- ($C_6H_3Cl_2$) | H | H | H | H | Me | 399 |

TABLE 1-continued

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 73 | CO$_2$Me | 2,4-dimethylphenyl, C$_8$H$_9$ | H | H | H | H | Et | 372 |
| 74 | CO$_2$Me | 4-(trifluoromethyl)phenyl, C$_7$H$_4$F$_3$ | H | H | H | H | Me | 398 |
| 75 | CO$_2$Me | 6-methylnaphthalen-2-yl, C$_{11}$H$_9$ | H | H | H | H | Me | 394 |

TABLE 1-continued

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 76 | $CO_2Me$ | 4-isopropylphenyl, $C_9H_{11}$ | H | H | H | H | Me | 372 |
| 77 | $CO_2Me$ | 3,5-dimethylphenyl, $C_8H_9$ | H | $NO_2$ | H | H | Me | 403 |
| 78 | $CO_2Me$ | 3,5-dimethylphenyl, $C_8H_9$ | H | H | $NO_2$ | H | Me | 403 |

TABLE 1-continued
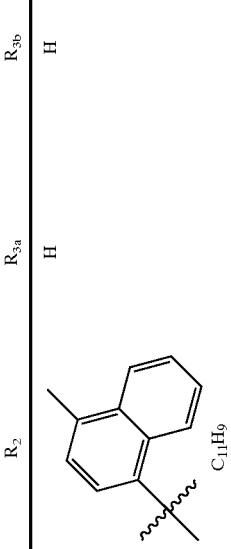
| No. | R₁ | R₂ | R₃ₐ | R₃ᵦ | R₃c | R₃d | R₄ | MS (M + 1) |
|---|---|---|---|---|---|---|---|---|
| 79 | CO₂Me | 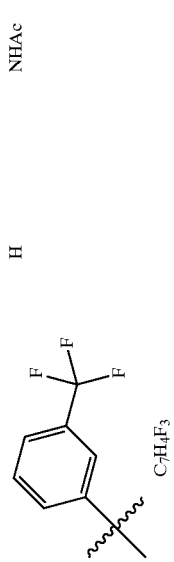 C₁₁H₉ | H | H | H | H | Me | 394 |
| 80 | CO₂Me | 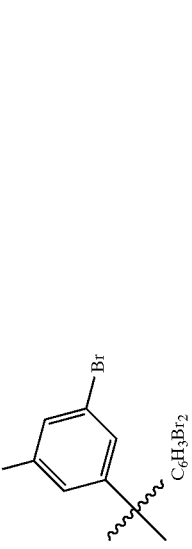 C₇H₄F₃ | H | NHAc | H | H | Me | 455 |
| 81 | CO₂Me |  C₆H₃Br₂ | H | H | H | H | Me | 488 |

TABLE 1-continued
Ia
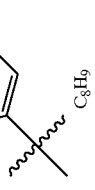
| No. | R₁ | R₂ | R₃ₐ | R₃ᵦ | R₃c | R₃d | R₄ | MS (M + 1) |
|---|---|---|---|---|---|---|---|---|
| 82 | CO₂Me | 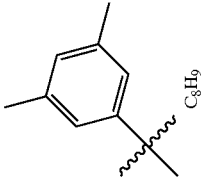 C₈H₉ | H | NH₂ | H | H | Me | 373 |
| 83 | CO₂Me | C₈H₉ | H | H | NH₂ | H | Me | 373 |
| 84 | CO₂Me | 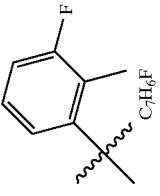 C₇H₆F | H | H | H | H | Me | 362 |

TABLE 1-continued
| No. | R₁ | R₂ | R₃ₐ | R₃ᵦ | R₃ᵧ | R₃d | R₄ | MS (M + 1) |
|---|---|---|---|---|---|---|---|---|
| 85 | $CO_2Me$ | 3-BrC₆H₄- (C₆H₄Br) | H | H | H | H | Me | 431 (M + 23) |
| 86 | $CO_2Me$ | 1-naphthyl (C₁₀H₇) | H | H | H | H | Me | 380 (M + 23) |
| 87 | $CO_2Me$ | 4-Me-naphthyl (C₁₁H₉) | H | $NO_2$ | H | H | Me | 439 |

TABLE 1-continued
| No. | R₁ | R₂ | R₃ₐ | R₃ᵦ | R₃ᵧ | R₃d | R₄ | MS (M+1) |
|---|---|---|---|---|---|---|---|---|
| 88 | CO₂Me | 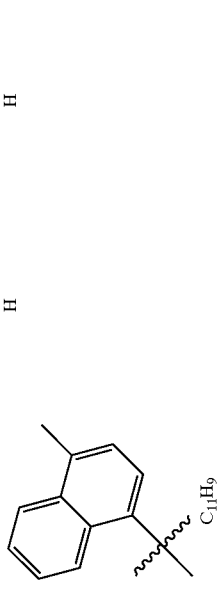 C₁₁H₉ | H | H | NO₂ | H | Me | 439 |
| 89 | CO₂Me | 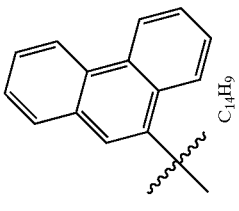 C₁₄H₉ | H | H | H | H | Me | 430 |
| 90 | CO₂Me | 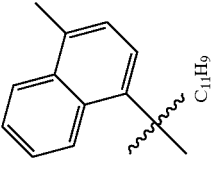 C₁₁H₉ | H | NH₂ | H | H | Me | 409 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 91 | CO₂Me | 4-methylnaphthyl, C₁₁H₉ | H | H | NH₂ | H | Me | 409 |
| 92 | CH₂C(=O)OCH₂CN, C₄H₄NO₂ | 2,4-dimethylphenyl, C₈H₉ | H | H | H | H | Me | 397 |
| 93 | CN | 2,4-dimethylphenyl, C₈H₉ | H | H | H | H | Me | 325 |

TABLE 1-continued
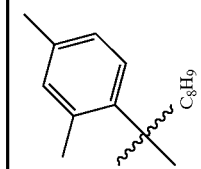
Ia
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 94 | $CO_2Me$ | 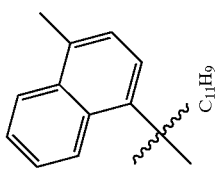 $C_8H_9$ | H | H | H | H | $NH_2$ | 359 |
| 95 | $CO_2Me$ | 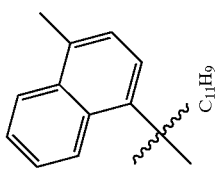 $C_{11}H_9$ | H | H | H | H | $NH_2$ | 395 |
| 96 | $CO_2H$ | 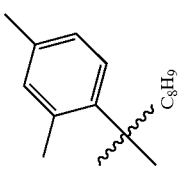 $C_8H_9$ | H | H | H | H | Me | 344 |

TABLE 1-continued
Ia
| No. | R1 | R2 | R3a | R3b | R3c | R3d | R4 | MS (M + 1) |
|---|---|---|---|---|---|---|---|---|
| 97 | 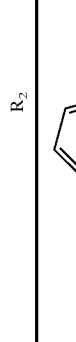 C4H4NO2 | 4-methylnaphthalen-1-yl, C11H9 | H | H | H | H | Me | 433 |
| 98 | CN | 4-methylnaphthalen-1-yl, C11H9 | H | H | H | H | Me | 361 |
| 99 | 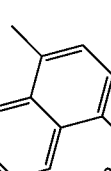 C2H5O2 | benzo[1,3]dioxol-5-yl, C7H5O2 | H | H | H | H | C2H2O2 | 358 |

TABLE 1-continued
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 100 | C$_2$H$_2$O$_2$ | C$_8$H$_{10}$N | H | H | H | H | C$_2$H$_2$O$_2$ | 357 |
| 101 | C$_2$H$_2$O$_2$ | Ph | H | H | H | H | C$_2$H$_2$O$_2$ | 314 |
| 102 | C$_2$H$_2$O$_2$ | C$_6$H$_6$NO$_2$ | H | H | H | H | C$_2$H$_2$O$_2$ | 361 |

TABLE 1-continued
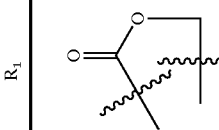
Ia
| No. | R₁ | R₂ | R₃ₐ | R₃ᵦ | R₃c | R₃d | R₄ | MS (M + 1) |
|---|---|---|---|---|---|---|---|---|
| 103 | 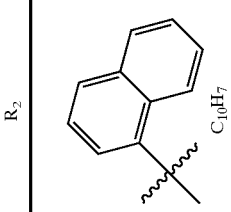 C₂H₂O₂ | 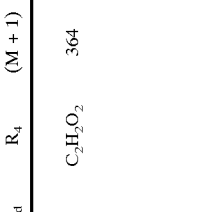 C₁₀H₇ | H | H | H | H | C₂H₂O₂ | 364 |
| 104 | 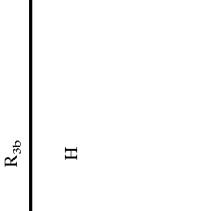 C₂H₂O₂ | 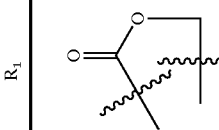 C₈H₉ | H | H | H | H | C₂H₂O₂ | 342 |
| 105 | CO₂H | 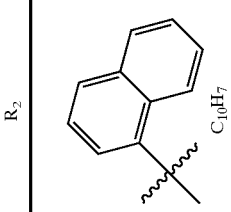 C₁₁H₉ | H | H | H | H | Me | 380 |

TABLE 1-continued
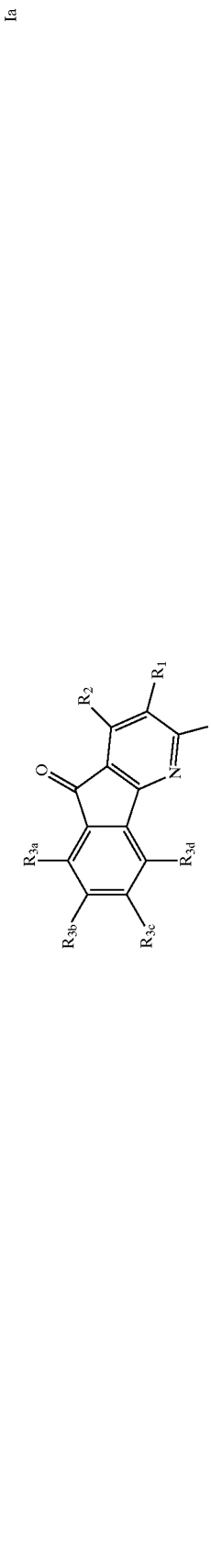
| No. | R₁ | R₂ | R₃ₐ | R₃ᵦ | R₃c | R₃d | R₄ | MS (M + 1) |
|---|---|---|---|---|---|---|---|---|
| 106 | CONH₂ | ![2,4-dimethylphenyl-C₈H₉] | H | H | H | H | Me | 343 |
| 107 | CONHMe | ![2,4-dimethylphenyl-C₈H₉] | H | H | H | H | Me | 357 |
| 108 | CONMe₂ | ![2,4-dimethylphenyl-C₈H₉] | H | H | H | H | Me | 371 |

TABLE 1-continued

Ia: fluorenone-pyridine core with substituents $R_1, R_2, R_4$ on pyridine ring and $R_{3a}, R_{3b}, R_{3c}, R_{3d}$ on benzene ring.

| No. | $R_1$ | $R_2$ | $R_{3a}$ | $R_{3b}$ | $R_{3c}$ | $R_{3d}$ | $R_4$ | MS (M+1) |
|---|---|---|---|---|---|---|---|---|
| 109 | methyl lactone, $C_2H_2O_2$ | 4-methylnaphthalen-1-yl, $C_{11}H_9$ | H | H | H | H | $C_2H_2O_2$ | 378 |
| 110 | methyl lactone, $C_2H_2O_2$ | 2-methylphenyl, $C_7H_7$ | H | H | H | H | $C_2H_2O_2$ | 328 |
| 111 | methyl lactone, $C_2H_2O_2$ | 4-isopropylphenyl, $C_9H_{11}$ | H | H | H | H | $C_2H_2O_2$ | 356 |

TABLE 1-continued
Ia
| No. | R₁ | R₂ | R₃ₐ | R₃ᵦ | R₃𝒸 | R₃ᵈ | R₄ | MS (M + 1) |
|---|---|---|---|---|---|---|---|---|
| 112 | 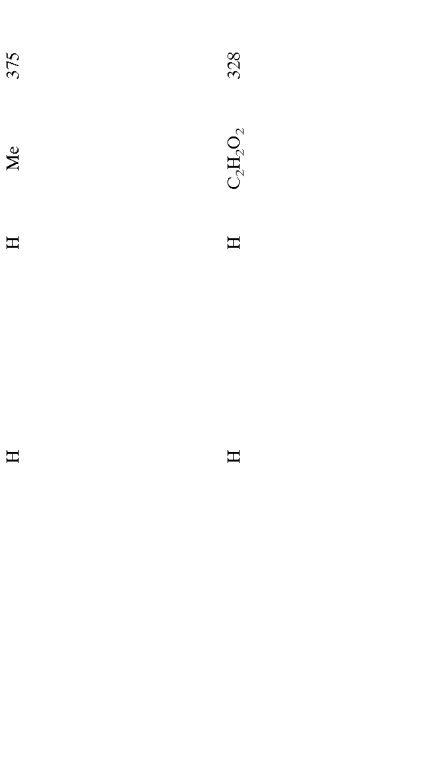 C₂H₂O₂ | C₇H₇ | H | H | H | H | C₂H₂O₂ | 328 |
| 113 | CO₂Me | C₆H₄NO₂ | H | H | H | H | Me | 375 |
| 114 | C₂H₂O₂ | C₇H₇ | H | H | H | H | C₂H₂O₂ | 328 |

TABLE 1-continued
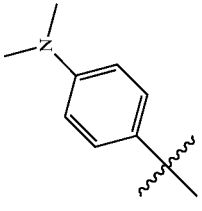
Ia
| No. | R1 | R2 | R3a | R3b | R3c | R3d | R4 | MS (M + 1) |
|---|---|---|---|---|---|---|---|---|
| 115 | CO2Me | 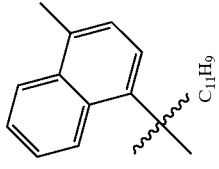 C8H10N | H | H | H | H | Me | 373 |
| 116 | CONH2 | C11H9 | H | H | H | H | Me | 379 |
| 117 | C2H2O2 | 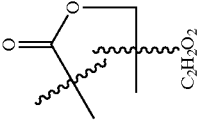 C9H6N | H | H | H | H | C2H2O2 | 365 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 118 | CO₂Me | 3-nitrophenyl (C₆H₄NO₂) | H | H | H | H | Me | 375 |
| 119 | CONHMe | 4-methylnaphthyl (C₁₁H₉) | H | H | H | H | Me | 393 |
| 120 | CONMe₂ | 4-methylnaphthyl (C₁₁H₉) | H | H | H | H | Me | 407 |

TABLE 1-continued

Ia structure with R₁, R₂, R₃ₐ, R₃ᵦ, R₃ᵧ, R₃ᵨ, R₄ substituents on the fluorenone-pyridine core.

| No. | R₁ | R₂ | R₃ₐ | R₃ᵦ | R₃ᵧ | R₃ᵨ | R₄ | MS (M + 1) |
|---|---|---|---|---|---|---|---|---|
| 121 | CO₂Me | quinolin-4-yl (C₉H₆N) | H | H | H | H | Me | 381 |
| 122 | CO₂Me | 5-methylnaphthalen-1-yl (C₁₁H₉) | H | Cl | Cl | H | Me | 463 |
| 123 | CO₂Me | 3,5-dimethylphenyl (C₈H₉) | H | Cl | Cl | H | Me | 427 |

TABLE 1-continued
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 124 | CO$_2$Me |  C$_9$H$_6$N | H | H | H | H | Me | 381 |
| 125 | CO$_2$Et | 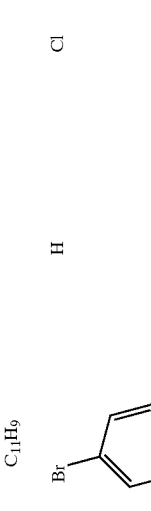 C$_{11}$H$_9$ | H | H | H | H | Me | 408 |
| 126 | CO$_2$Me |  C$_6$H$_3$Br$_2$ | H | Cl | Cl | H | Me | 555 |

TABLE 1-continued

Ia

| No. | R₁ | R₂ | R₃ₐ | R₃ᵦ | R₃꜀ | R₃ᵈ | R₄ | MS (M + 1) |
|---|---|---|---|---|---|---|---|---|
| 127 | CO₂Me | 3,5-dimethylphenyl, C₈H₉ | Cl | H | H | Cl | Me | 427 |
| 128 | CO₂Me | benzo[1,3]dioxol-5-yl with NHOH(C=O), C₇H₆NO₄ | H | H | H | H | Me | 421 |
| 129 | CO₂Me | 3,5-dibromophenyl, C₆H₃Br₂ | Cl | H | H | Cl | Me | 558 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 130 | CO₂Me | 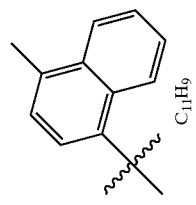 C₆H₆N | H | H | H | H | Me | 345 |
| 131 | CO₂Et | 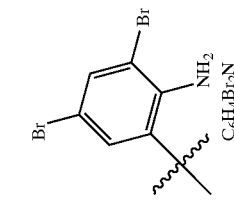 C₁₁H₉ | H | Cl | Cl | H | Me | 477 |
| 132 | CO₂Me |  C₆H₄Br₂N | H | H | H | H | Me | 503 |

TABLE 1-continued
Ia
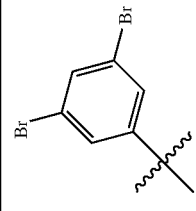
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 133 | Ac | 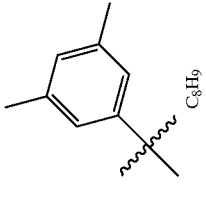 $C_6H_3Br_2$ | H | H | H | H | Me | 472 |
| 134 | Ac | 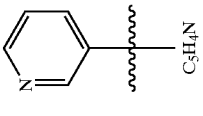 $C_8H_9$ | H | H | H | H | Me | 342 |
| 135 | $CO_2Me$ |  $C_5H_4N$ | H | H | H | H | Me | 331 |

TABLE 1-continued

Ia (structure shown: tricyclic indenopyridinone with substituents R1, R2, R3a, R3b, R3c, R3d, R4)

| No. | R1 | R2 | R3a | R3b | R3c | R3d | R4 | MS (M + 1) |
|---|---|---|---|---|---|---|---|---|
| 136 | –C(Me)-C(=O)-O-CH₂CH₂-C≡N (C₄H₄NO₂) | 3,5-dibromophenyl-C(Me)- (C₆H₃Br₂) | H | H | H | H | Me | 527 |
| 137 | –C(Me)-C(=O)-O-CH₂CH₂-C≡N (C₄H₄NO₂) | 3,5-dimethylphenyl-C(Me)- (C₈H₉) | H | H | H | H | Me | 397 |

TABLE 1-continued

Ia

[Structure: tricyclic fluorenone-pyridine core with substituents R1, R2, R3a, R3b, R3c, R3d, R4]

| No. | R1 | R2 | R3a | R3b | R3c | R3d | R4 | MS (M + 1) |
|---|---|---|---|---|---|---|---|---|
| 138 | CO₂Me | 3,4-dihydroxyphenyl (C₆H₅O₂) | H | H | H | H | Me | 362 |
| 139 | CO₂H | 3,5-dibromophenyl (C₆H₃Br₂) | H | H | H | H | Me | 474 |
| 140 | CO₂H | 3,5-dimethylphenyl (C₈H₉) | H | H | H | H | Me | 344 |

TABLE 1-continued

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 141 | $CO_2Me$ | 3-hydroxyphenyl-CH(CH$_3$)- ($C_6H_5O$) | H | H | H | H | Me | 346 |
| 142 | $CO_2Me$ | 2-naphthyl-CH(CH$_3$)- ($C_{10}H_7$) | H | H | H | H | Me | 380 |
| 143 | $CO_2Me$ | 4-(hexyloxy)phenyl- with (CH$_2$)$_5$CH$_3$ ($C_{16}H_{25}O$) | H | H | H | H | Me | 486 |

TABLE 1-continued

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 144 | CO$_2$Me | C$_{13}$H$_{11}$O (benzyloxyphenyl) | H | H | H | H | Me | 436 |
| 145 | CO$_2$Me | C$_7$H$_5$Br$_2$O (dibromo-methoxyphenyl) | H | H | H | H | Me | 518 |
| 146 | C$_4$H$_4$NO$_2$ (cyanoethyl ester) | C$_7$H$_5$Br$_2$O (dibromo-methoxyphenyl) | H | H | H | H | Me | 557 |

TABLE 1-continued
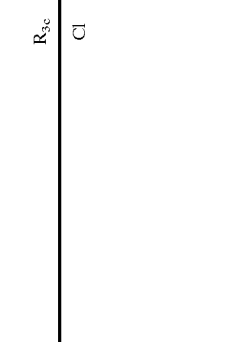
Ia
| No. | R₁ | R₂ | R₃ₐ | R₃ᵦ | R₃c | R₃d | R₄ | MS (M + 1) |
|---|---|---|---|---|---|---|---|---|
| 147 | <br>C₄H₄NO₂ | <br>C₈H₉ | H | Cl | Cl | H | Me | 466 |
| 148 | CO₂Et | —NHPh | H | H | H | H | Me | 359 |
| 149 | CO₂Me | <br>C₇H₇O | H | H | H | H | Me | 360 |
| 150 | CO₂Me | <br>C₆H₃Br₂O | H | H | H | H | Me | 504 |

TABLE 1-continued
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 151 |  C$_4$H$_4$NO$_2$ |  C$_9$H$_6$N | H | H | H | H | Me | 420 |
| 152 | C$_3$H$_5$O$_3$ |  C$_6$H$_3$Br$_2$O | H | H | H | H | Me | 534 |
| 153 |  C$_4$H$_4$NO$_2$ |  C$_6$H$_5$O | H | H | H | H | Me | 385 |

TABLE 1-continued

| No. | R1 | R2 | R3a | R3b | R3c | R3d | R4 | MS (M + 1) |
|---|---|---|---|---|---|---|---|---|
| 154 | -C(O)-NH-OMe, C2H4NO2 | 3,5-dimethylphenyl, C8H9 | H | H | H | H | Me | 373 |
| 155 | -C(O)O-CH2CH2-CN, C4H4NO2 | 3,5-dibromophenyl, C6H3Br2 | H | H | NO2 | H | Me | 574 |
| 156 | CO2Me | 4-methylnaphthyl, C11H9 | H | Br | H | H | Me | 473 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 157 | CO₂Me | 4-methylnaphthalen-1-yl, C₁₁H₉ | H | H | Br | H | Me | 473 |
| 158 | 2-cyanoethyl ester (C₄H₄NO₂) | quinolin-4-yl, C₉H₆N | H | Cl | Cl | H | Me | 489 |
| 159 | 2-cyanoethyl ester (C₄H₄NO₂) | 3,5-dibromo-4-hydroxyphenyl, C₆H₃Br₂O | H | H | NO₂ | H | Me | 590 |

TABLE 1-continued
| No. | R₁ | R₂ | R₃ₐ | R₃ᵦ | R₃꜀ | R₃d | R₄ | MS (M + 1) |
|---|---|---|---|---|---|---|---|---|
| 160 |  C₃H₅O₃ |  C₉H₆N | H | H | H | H | Me | 411 |
| 161 | CO₂Me |  C₈H₉ | H | Br | H | H | Me | 436 |
| 162 | CO₂Me |  C₈H₉ | H | H | Br | H | Me | 438 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 163 | CO₂Me | 3,5-dimethylphenyl (C₈H₉) | H | Br | Br | H | Me | 516 |
| 164 | 2-cyanoethyl ester (C₄H₄NO₂) | 3,5-dibromophenyl (C₆H₃Br₂) | H | Cl | Cl | H | Me | 597 |
| 165 | 2-hydroxyethyl ester (C₃H₅O₃) | quinolin-4-yl (C₉H₆N) | H | Cl | Cl | H | Me | 480 |

TABLE 1-continued

Ia (structure shown with R₁, R₂, R₃ₐ, R₃ᵦ, R₃c, R₃d, R₄ substituents on the indeno-pyridinone core)

| No. | R₁ | R₂ | R₃ₐ | R₃ᵦ | R₃c | R₃d | R₄ | MS (M + 1) |
|---|---|---|---|---|---|---|---|---|
| 166 | CO₂Me | 4-methylnaphthalen-1-yl, C₁₁H₉ | H | Br | Br | H | Me | 552 |
| 167 | CO₂Et | 3,5-dimethylphenyl, C₈H₉ | H | Br | Br | H | Me | 530 |
| 168 | CO₂Me | 3,5-dibromo-4-hydroxyphenyl, C₆H₃Br₂O | F | H | H | F | Me | 540 |

TABLE 1-continued

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 169 | CO$_2$Me | 2,6-dibromo-4-hydroxyphenyl-C(CH$_3$)- (C$_6$H$_3$Br$_2$O) | H | H | NO$_2$ | H | Me | 551 |
| 170 | CO$_2$Me | 2,6-dibromo-4-hydroxyphenyl-C(CH$_3$)- (C$_6$H$_3$Br$_2$O) | H | Cl | Cl | H | Me | 573 |
| 171 | -C(CH$_3$)(CO-O-CH$_2$CH$_2$CN)- (C$_4$H$_4$NO$_2$) | 3,5-dimethylphenyl (C$_8$H$_9$) | H | H | NO$_2$ | H | Me | 444 |

TABLE 1-continued
Ia
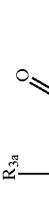
| No. | R₁ | R₂ | R₃ₐ | R₃ᵦ | R₃c | R₃d | R₄ | MS (M + 1) |
|---|---|---|---|---|---|---|---|---|
| 172 | 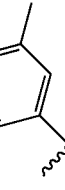 C₄H₄NO₂ | 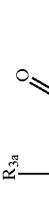 C₈H₉ | H | NO₂ | H | H | Me | 444 |
| 173 | CO₂Me | 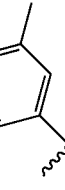 C₈H₉ | F | H | H | F | Me | 394 |
| 174 |  C₄H₄NO₂ |  C₈H₉ | F | H | H | F | Me | 433 |

TABLE 1-continued
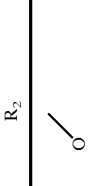
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 175 | CO$_2$Me | 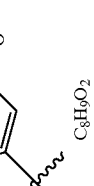 3,5-dimethoxyphenyl, C$_8$H$_9$O$_2$ | H | Br | Br | H | Me | 548 |
| 176 | CO$_2$Me | 4-cyanophenyl, C$_7$H$_4$N | H | H | H | H | Me | 355 |
| 177 | CO$_2$Me | 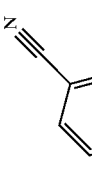 4-hydroxy-3,5-dimethylphenyl, C$_8$H$_9$O | H | NO$_2$ | H | H | Me | 421 |

TABLE 1-continued

[Structure: Ia — indeno-pyridinone core with substituents $R_1, R_2, R_4$ on pyridine ring, $R_{3a}, R_{3b}, R_{3c}, R_{3d}$ on benzene ring, with carbonyl (O=)]

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 178 | $CO_2Me$ | 4-OH-3,5-diMe-C$_6$H$_2$-C(Me)$_2$- ($C_8H_9O$) | H | H | $NO_2$ | H | Me | 453 (M + 23) |
| 179 | $CO_2Me$ | 4-OH-3,5-diMe-C$_6$H$_2$-C(Me)$_2$- ($C_8H_9O$) | H | Cl | Cl | H | Me | 443 |
| 180 | CN | 4-OH-3,5-diMe-C$_6$H$_2$-C(Me)$_2$- ($C_8H_9O$) | H | H | H | H | Me | 341 |

TABLE 1-continued
Ia
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 181 | $CO_2Me$ |  $C_6H_3I_2O$ | H | H | H | H | Me | 598 |
| 182 | $CO_2Me$ |  $C_6H_3F_2$ | H | Cl | Cl | H | Me | 435 |
| 183 | $CO_2Et$ |  $C_8H_{10}N$ | H | H | H | H | Me | 387 |

TABLE 1-continued
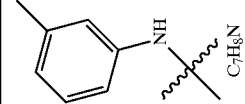
| No. | R₁ | R₂ | R₃ₐ | R₃ᵦ | R₃c | R₃d | R₄ | MS (M + 1) |
|---|---|---|---|---|---|---|---|---|
| 184 | CO₂Et | 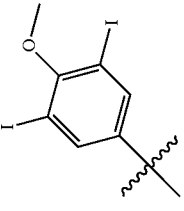 C₇H₈N | H | H | H | H | Me | 373 |
| 185 | CO₂Me | 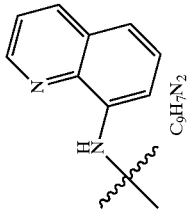 C₇H₅I₂O | H | H | H | H | Me | 612 |
| 186 | CO₂Et |  C₉H₇N₂ | H | H | H | H | Me | 410 |

TABLE 1-continued
Ia
| No. | R₁ | R₂ | R₃ₐ | R₃ᵦ | R₃c | R₃d | R₄ | MS (M + 1) |
|---|---|---|---|---|---|---|---|---|
| 187 | CO₂Me |  C₆H₃I₂O | H | H | NO₂ | H | Me | 345 |
| 188 | CO₂Me |  C₆H₃I₂O | H | Cl | Cl | H | Me | 668 |
| 189 | CO₂Me |  C₆H₃F₂ | H | H | NO₂ | H | Me | 413 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 190 | CO₂H | 3,5-dibromophenyl (C₆H₃Br₂) | H | Cl | Cl | H | Me | 544 |
| 191 | CN | 4-hydroxy-3,5-diiodophenyl (C₆H₃I₂O) | H | H | H | H | Me | 565 |
| 192 | CO₂Me | 4-hydroxy-3,5-dibromophenyl (C₆H₃Br₂O) | H | Br | H | H | Me | 606 (M + 23) |

TABLE 1-continued
Ia
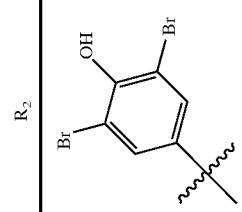
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 193 | $CO_2Me$ | 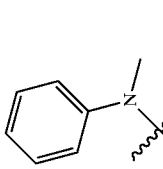 2,6-dibromo-4-hydroxyphenyl-C(CH3)2- $C_6H_3Br_2O$ | H | H | Br | H | Me | 584 |
| 194 | $CO_2Et$ | N-methyl-N-phenylamino-C(CH3)2- $C_7H_8N$ | H | H | H | H | Me | 373 |
| 195 | $CO_2Et$ | 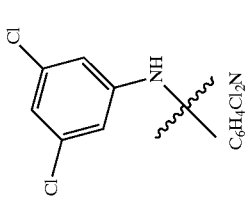 3,5-dichlorophenyl-NH-C(CH3)2- $C_6H_4Cl_2N$ | H | H | H | H | Me | 427 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 196 | CO₂Et | 2,6-dibromo-4-hydroxyphenyl-C(CH₃)₂- (C₆H₃Br₂O) | H | Cl | Cl | H | Me | 587 |
| 197 | CO₂Et | 3-bromophenyl-NH-C(CH₃)₂- (C₆H₅BrN) | H | H | H | H | Me | 437 |
| 198 | CO₂Et | 3-methoxyphenyl-NH-C(CH₃)₂- (C₇H₈NO) | H | H | H | H | Me | 389 |

TABLE 1-continued
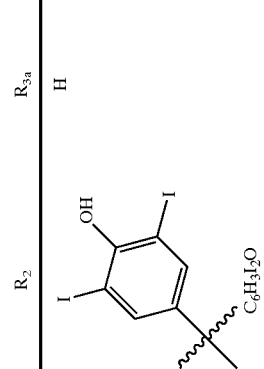
| No. | R₁ | R₂ | R₃ₐ | R₃ᵦ | R₃c | R₃d | R₄ | MS (M + 1) |
|---|---|---|---|---|---|---|---|---|
| 199 | CO₂Et | 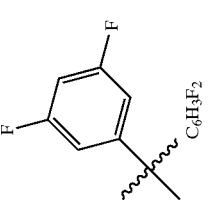
2,6-diiodo-4-hydroxyphenyl
C₆H₃I₂O | H | H | H | H | Me | 612 |
| 200 | CO₂Et | 3,5-difluorophenyl
C₆H₃F₂ | H | Cl | Cl | H | Me | 449 |
| 201 | CO₂Me | quinolin-4-yl
C₉H₆N | H | Cl | Cl | H | Me | 450 |

TABLE 1-continued
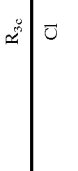
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 202 | CO$_2$Me |  C$_7$H$_5$F$_2$O | H | Cl | Cl | H | Me | 465 |
| 203 | CO$_2$Me | C$_7$H$_5$F$_2$O | H | H | H | H | Me | 396 |
| 204 | CO$_2$Me | C$_8$H$_9$ | H |  C$_4$H$_6$NO$_3$ | H | H | Me | 473 |

TABLE 1-continued
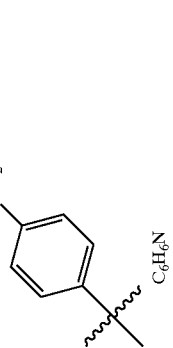
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 205 | CO$_2$Me | 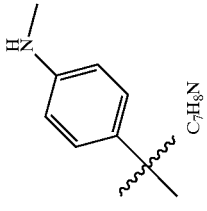 C$_6$H$_6$N | H | H | H | H | Me | 345 |
| 206 | CO$_2$Me | 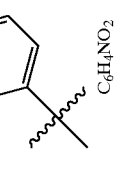 C$_7$H$_8$N | H | H | H | H | Me | 359 |
| 207 | CO$_2$Me |  C$_6$H$_4$NO$_2$ | H | Cl | Cl | H | Me | 444 |

TABLE 1-continued
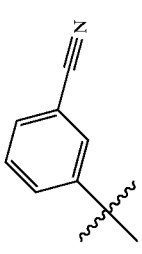
| No. | R₁ | R₂ | | R₃ₐ | R₃ᵦ | R₃c | R₃d | R₄ | MS (M + 1) |
|---|---|---|---|---|---|---|---|---|---|
| 208 | CO₂Me | 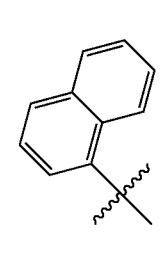 | C₇H₄N | H | H | H | H | Me | 355 |
| 209 | CO₂H | 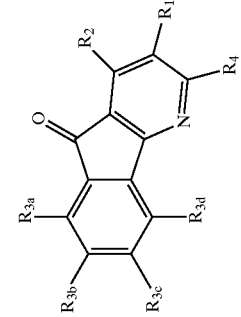 | C₁₀H₇ | H | H | H | H | Me | 366 |
| 210 | CO₂Me | 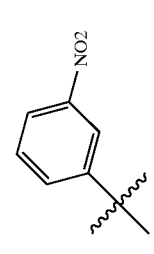 | C₆H₄NO₂ | H | Cl | Cl | H | Me | 444 |
| 211 | CO₂Me | 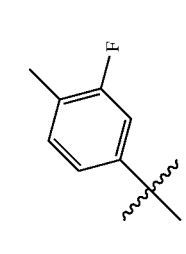 | C₇H₆F | H | Cl | Cl | H | Me | 430 |

TABLE 1-continued
Ia
| No. | R₁ | R₂ | R₃ₐ | R₃ᵦ | R₃ᵧ | R₃ᵨ | R₄ | MS (M + 1) |
|---|---|---|---|---|---|---|---|---|
| 212 | CO₂Me | 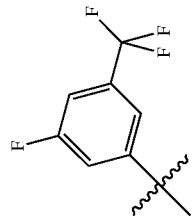 C₇H₃F₄ | H | H | H | H | Me | 416 |
| 213 | CO₂Me | 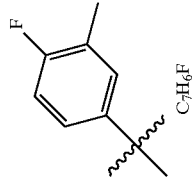 C₇H₆F | H | Cl | Cl | H | Me | 430 |
| 214 | CO₂Me | 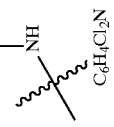 C₆H₄Cl₂N | H | H | H | H | Me | 413 |

TABLE 1-continued

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 215 | CO$_2$Me | 3,5-dimethylphenyl (C$_8$H$_9$) | H | OMe | OMe | H | Me | 418 |
| 216 | CO$_2$Me | 4-methylnaphthalen-1-yl (C$_{11}$H$_9$) | H | OMe | OMe | H | Me | 454 |
| 217 | CO$_2$Me | 3-fluoro-4-methylphenyl (C$_7$H$_6$F) | H | H | H | H | Me | 362 |

TABLE 1-continued
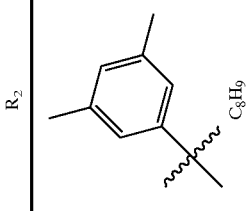
Ia
| No. | R₁ | R₂ | R₃ₐ | R₃ᵦ | R₃c | R₃d | R₄ | MS (M + 1) |
|---|---|---|---|---|---|---|---|---|
| 218 | CO₂Me | 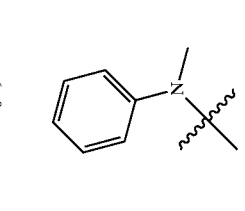 3,5-dimethylphenyl, C₈H₉ | H | $\underset{\text{C}_3\text{H}_6\text{NO}_2}{\text{HOOC-CH}_2\text{CH}_2\text{-HN-}}$ | H | H | Me | 445 |
| 219 | CO₂Me | 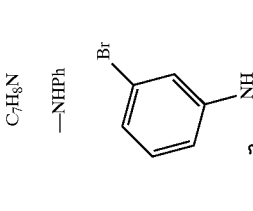 N-methyl-N-phenylamino, C₇H₈N | H | H | H | H | Me | 359 |
| 220 | CO₂Me | —NHPh | H | H | H | H | Me | 345 |
| 221 | CO₂Me |  3-bromophenylamino, C₆H₅BrN | H | H | H | H | Me | 423 |

TABLE 1-continued

Ia (structure shown with $R_1$, $R_2$, $R_{3a}$, $R_{3b}$, $R_{3c}$, $R_{3d}$, $R_4$ substituents on fluorenone-pyridine core)

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 222 | $CO_2Me$ | 2-Pyridyl | H | H | H | H | Me | 353 (M + 23) |
| 223 | $CO_2Me$ | 3,5-dichlorophenyl ($C_6H_3Cl_2$) | H | OMe | OMe | H | Me | 459 |
| 224 | $CO_2Me$ | 3-fluoro-5-(trifluoromethyl)phenyl ($C_7H_3F_4$) | H | Cl | Cl | H | Me | 485 |
| 225 | $CO_2Me$ | 6-methylpyridin-2-yl ($C_6H_6N$) | H | H | H | H | Me | 345 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 226 | CO₂Me |  C₆H₄NO₂ | H | H | NO₂ | H | Me | 420 |
| 227 | CO₂Me |  C₆H₄NO₂ | H | H | NO₂ | H | Me | 420 |
| 228 | CO₂Me |  C₇H₈N | H | H | H | H | Me | 359 |

TABLE 1-continued
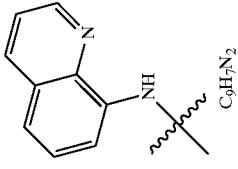
Ia
| No. | R₁ | R₂ | R₃ₐ | R₃ᵦ | R₃c | R₃d | R₄ | MS (M + 1) |
|---|---|---|---|---|---|---|---|---|
| 229 | CO₂Me | 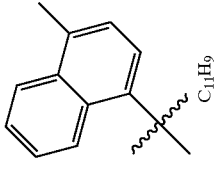 C₉H₇N₂ (8-quinolinyl-NH-C(Me)₂-) | H | H | H | H | Me | 396 |
| 230 | CO₂Me | 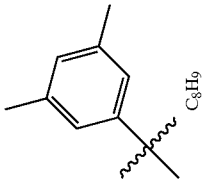 C₁₁H₉ (4-methylnaphthalen-1-yl-C(Me)₂-) | H | OH | OH | H | Me | 426 |
| 231 | CO₂Me | C₈H₉ (3,5-dimethylphenyl-C(Me)₂-) | H | H | F | H | Me | 376 |

TABLE 1-continued
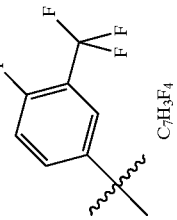
| No. | R₁ | R₂ | R₃ₐ | R₃ᵦ | R₃c | R₃d | R₄ | MS (M + 1) |
|---|---|---|---|---|---|---|---|---|
| 232 | CO₂Me | 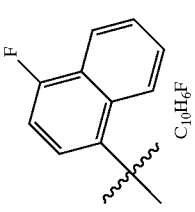 C₇H₃F₄ | H | H | NO₂ | H | Me | 461 |
| 233 | CO₂Me | 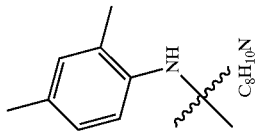 C₁₀H₆F | H | Cl | Cl | H | Me | 468 |
| 234 | CO₂Me |  C₈H₁₀N | H | H | H | H | Me | 373 |

TABLE 1-continued

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 235 | $CO_2Me$ | 3-methoxyphenyl-NH- ($C_7H_8NO$) | H | H | H | H | Me | 375 |
| 236 | $CO_2Me$ | 4-fluoronaphthyl ($C_{10}H_6F$) | H | $NO_2$ | H | H | Me | 443 |
| 237 | $CO_2Me$ | 4-fluoronaphthyl ($C_{10}H_6F$) | H | H | $NO_2$ | H | Me | 443 |

TABLE 1-continued
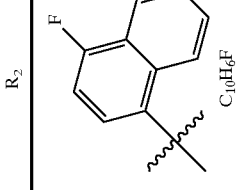
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 238 | CO$_2$Me | 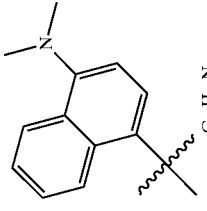 4-fluoronaphthyl, C$_{10}$H$_6$F | H | H | H | H | Me | 398 |
| 239 | CO$_2$Me | 4-(dimethylamino)naphthyl, C$_{12}$H$_{12}$N | H | Cl | Cl | H | Me | 491 |
| 240 | CO$_2$Me | 4-methylnaphthyl, C$_{11}$H$_9$ | H | 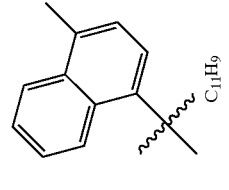 C$_4$H$_6$NO$_3$ | H | H | Me | 509 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 241 | CO₂Me |  3,5-dimethylphenyl, C₈H₉ | H | H | 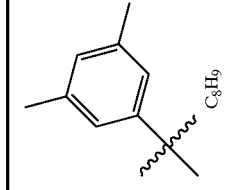 C₄H₆NO₃ | H | Me | 473 |
| 242 | CO₂Me |  naphthyl, C₁₁H₉ | H | H |  C₄H₆NO₃ | H | Me | 509 |
| 243 | CO₂Me |  C₄H₉ | H | H | H | H | Me | 310 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 244 | CO₂Me | 1-methylnaphthalen-4-yl, C₁₁H₉ | H | HOHN-C(O)-CH₂CH₂-C(O)-NH- (C₄H₇N₂O₃) | H | H | Me | 524 |
| 245 | CO₂Me | 3,5-dimethylphenyl, C₈H₉ | H | H | HOHN-C(O)-CH₂CH₂-C(O)-NH- (C₄H₇N₂O₃) | H | Me | 488 |
| 246 | CO₂Me | pent-4-en-2-yl, C₄H₇ | H | H | H | H | Me | 308 |
| 247 | CO₂Me | i-Pr | H | H | H | H | Me | 296 |

TABLE 1-continued

Ia

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 248 | $CO_2Me$ | Cyclohexyl | H | H | H | H | Me | 336 |
| 249 | $CO_2Me$ | Me | H | H | H | H | Me | 268 |
| 250 | $CO_2Me$ | 3,5-dimethylphenyl ($C_8H_9$) | H | H | H | H | Me | 474 |
| 251 | $CO_2Me$ | 3,5-dimethylphenyl ($C_8H_9$) | H | H | $C_4H_9N_2O_2$ (HOCH₂CH₂NHCH₂C(O)NH—) | H | Me | 487 |
| 252 | $CO_2Me$ | N-Morpholino | H | H | $C_5H_8NO_3$ (HOOCCH₂CH₂C(O)NH—) | H | Me | 339 |

TABLE 1-continued
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 253 | CO$_2$Me | 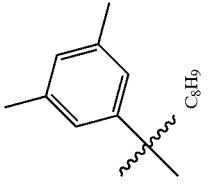 | H | H | H | H | Me | 337 |
| 254 | CO$_2$Me | 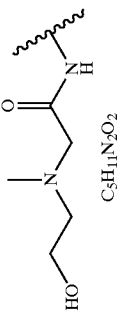 | H | H | 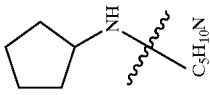 | H | Me | 488 |
| 255 | CO$_2$Me | 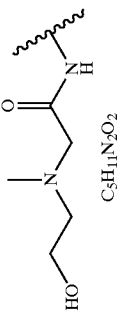 | H | 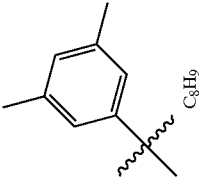 | H | H | Me | 474 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 256 | CO₂Me | 3,5-dimethylphenyl (C₈H₉) | H | piperazin-2-one-N-yl (C₄H₇N₂O) | H | H | Me | 456 |
| 257 | CO₂Me | 3,5-dimethylphenyl (C₈H₉) | H | NHCH₂CH₂OH (C₂H₄NO₂) | H | H | Me | 431 |
| 258 | CO₂Me | 3,5-dimethylphenyl (C₈H₉) | H | NHC(O)CH₂-morpholino (C₆H₁₁N₂O₂) | H | H | Me | 500 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 259 | CO₂Me | 3,5-dimethylphenyl (C₈H₉) | H | CH₂-piperazinyl-C(O)NH- (C₆H₁₂N₃O) | H | H | Me | 499 |
| 260 | CO₂Me | 3,5-dimethylphenyl (C₈H₉) | H | CH₂-imidazolyl-C(O)NH- (C₅H₆N₃O) | H | H | Me | 481 |
| 261 | CO₂Me | 3,5-dimethylphenyl (C₈H₉) | H | H | CH₂-morpholinyl-C(O)NH- (C₆H₁₁N₂O₂) | H | Me | 500 |

TABLE 1-continued
Ia
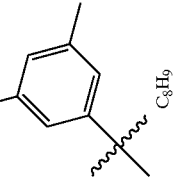
| No. | R₁ | R₂ | R₃ₐ | R₃ᵦ | R₃꜀ | R₃d | R₄ | MS (M + 1) |
|---|---|---|---|---|---|---|---|---|
| 262 | CO₂Me | 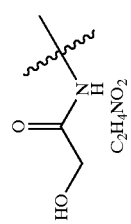 C₈H₉ | H | H | 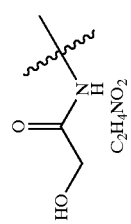 C₆H₁₂N₃O | H | Me | 499 |
| 263 | CO₂Me | 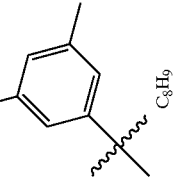 C₈H₉ | H | H | 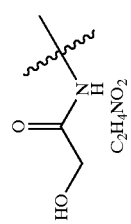 C₂H₄NO₂ | H | Me | 431 |

III. Biological Assays and Activity

The assay of phosphodiesterase activity follows the homogeneous SPA (scintillation proximity assay) format under the principle that linear nucleotides preferentially bind yttrium silicate beads in the presence of zinc sulfate.

In this assay, the enzyme converts radioactively tagged cyclic nucleotides (reaction substrate) to linear nucleotides (reaction product) which are selectively captured via ion chelation on a scintillant-containing bead. Radiolabeled product bound to the bead surface results in energy transfer to the bead scintillant and generation of a quantifiable signal. Unbound radiolabel fails to achieve close proximity to the scintillant and therefore does not generate any signal.

Specifically, enzyme was diluted in PDE buffer (50 mM pH 7.4 Tris, 8.3 mM $MgCl_2$, 1.7 mM EGTA) with 0.1% ovalbumin such that the final signal:noise (enzyme:no enzyme) ratio is 5–10. Substrate (2,8-$^3$H-cAMP or 8-$^3$H-cGMP, purchased from Amersham Pharmacia) was diluted in PDE (4, 5, 7A) buffer to 1 nCi per $\mu$l (or 1 $\mu$Ci/ml). For each test well, 48 $\mu$l of enzyme was mixed with 47 $\mu$l substrate and 5 $\mu$l test compound (or DMSO) in a white Packard plate, followed by shaking to mix and incubation for 15 minutes at room temperature. A 50 $\mu$l aliquot of evenly suspended yttrium silicate SPA beads in zinc sulfate was added to each well to terminate the reaction and capture the product. The plate was sealed using Topseal-S (Packard) sheets, and the beads were allowed to settle by gravity for 15–20 minutes prior to counting on a Packard TopCount scintillation counter using a $^3$H glass program with color quench correction. Output was in color quench-corrected dpm.

Test compounds were diluted in 100% DMSO to a concentration 20× final assay concentration. DMSO vehicle alone was added to uninhibited control wells. Inhibition (%) was calculated as follows:

Nonspecific binding (NSB)=the mean of $CPM$ of the substrate+buffer+DMSO wells

Total Binding (TB)=the mean of the enzyme+substrate+DMSO wells $$\% \text{ Inhibition listed in Table } 1 = \left(1 - \left(\frac{\text{Sample } CPM - NSB}{TB - NSB}\right)\right) \times 100$$

The $IC_{50}$ values were calculated using the Deltagraph 4-parameter curve-fitting program. The $IC_{50}$ and % Inhibition data on PDE 4, 5, and 7A are listed for the indicated compounds in Table 2 below.

TABLE 2

Ia

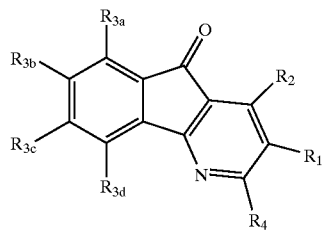

| No. | $R_1$ | $R_2$ | $R_{3a}$ | $R_{3b}$ | $R_{3c}$ | $R_{3d}$ | $R_4$ | MS (M+1) | $IC_{50}$ ($\mu$M)/% inh. @ $\mu$M PDE7A | PDE4 | PDE5 |
|---|---|---|---|---|---|---|---|---|---|---|---|
| 6 | $CO_2H$ | 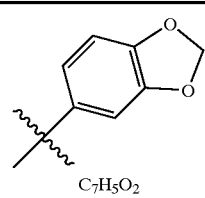 $C_7H_5O_2$ | H | H | H | H | Me | 360 | 45% @ 20 | 49% @ 5 | |
| 51 | $CO_2Me$ | 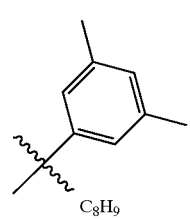 $C_8H_9$ | H | H | H | H | Me | 358 | 0.055 | 0.353 | 2.7 |
| 56 | $CO_2Et$ | 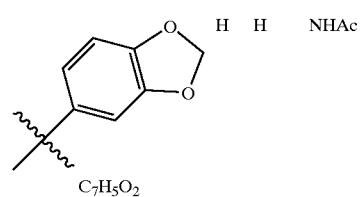 $C_7H_5O_2$ | H | H | NHAc | H | Me | 445 | 0.074 | 0.333 | 2.5 |

TABLE 2-continued
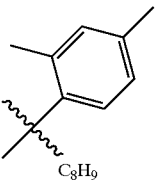
| No. | R₁ | R₂ | R₃ₐ | R₃ᵦ | R₃c | R₃d | R₄ | MS (M + 1) | IC₅₀ (μM)/% inh. @ μM PDE7A | PDE4 | PDE5 |
|---|---|---|---|---|---|---|---|---|---|---|---|
| 70 | CO₂Et | 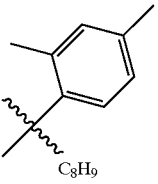 C₈H₉ | H | H | H | H | i-Pr | 400 | 2.11 | | |
| 73 | CO₂Me | 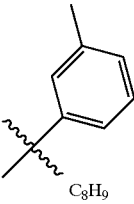 C₈H₉ | H | H | H | H | Et | 372 | 1.54 | | 0.998 |
| 82 | CO₂Me | 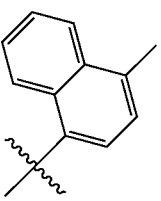 C₈H₉ | H | NH₂ | H | H | Me | 373 | 0.021 | 0.204 | 1.11, 0.864 |
| 90 | CO₂Me | 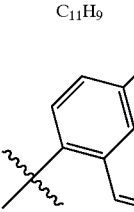 C₁₁H₉ | H | NH₂ | H | H | Me | 409 | 0.005 | 0.237, 0.172 | 2.33 |
| 98 | CN | 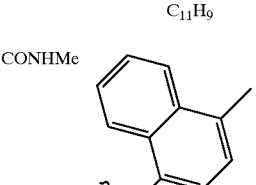 C₁₁H₉ | H | H | H | H | Me | 361 | 1.13 | | |
| 119 | CONHMe |  C₁₁H₉ | H | H | H | H | Me | 393 | 0.658 | 41% @ 20 | |

TABLE 2-continued
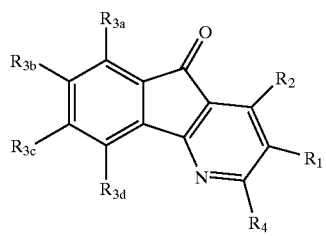
Ia
| No. | $R_1$ | $R_2$ | $R_{3a}$ | $R_{3b}$ | $R_{3c}$ | $R_{3d}$ | $R_4$ | MS (M+1) | IC$_{50}$ ($\mu$M)/% inh. @ $\mu$M PDE7A | PDE4 | PDE5 |
|---|---|---|---|---|---|---|---|---|---|---|---|
| 133 | Ac | C$_6$H$_3$Br$_2$ (3,5-diBr-phenyl) | H | H | H | H | Me | 472 | 1.54 | | |
| 134 | Ac | C$_8$H$_9$ (3,5-diMe-phenyl) | H | H | H | H | Me | 342 | 1.14 | | |
| 169 | CO$_2$Me | C$_6$H$_3$Br$_2$O (3,5-diBr-4-OH-phenyl) | H | H | NO$_2$ | H | Me | 551 | 0.0053 | | 0.184 |
| 170 | CO$_2$Me | C$_6$H$_3$Br$_2$O (3,5-diBr-4-OH-phenyl) | H | Cl | Cl | H | Me | 573 | 0.0087 | | 0.557 |
| 190 | CO$_2$H | C$_6$H$_3$Br$_2$ (3,5-diBr-phenyl) | H | Cl | Cl | H | Me | 544 | 5.9 | | |

TABLE 2-continued
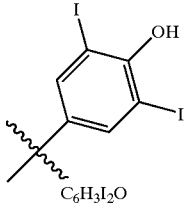
| No. | R₁ | R₂ | R₃ₐ | R₃ᵦ | R₃c | R₃d | R₄ | MS (M + 1) | IC₅₀ (μM)/% inh. @ μM | | |
|---|---|---|---|---|---|---|---|---|---|---|---|
| | | | | | | | | | PDE7A | PDE4 | PDE5 |
| 191 | CN | 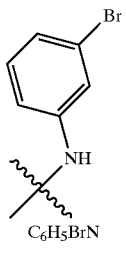 C₆H₃I₂O | H | H | H | H | Me | 565 | 0.593 | | |
| 197 | CO₂Et | 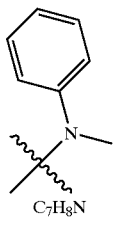 C₆H₅BrN | H | H | H | H | Me | 437 | 0.728 | 69% @ 5 | 0.362 |
| 219 | CO₂Me | 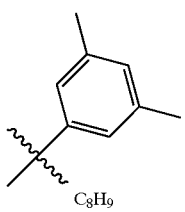 C₇H₈N | H | H | H | H | Me | 359 | 0.964 | 61% @ 5 | 1.1 |
| 220 | CO₂Me | —NHPh | H | H | H | H | Me | 345 | 0.084 | 1.8 | 0.637 |
| 241 | CO₂Me | 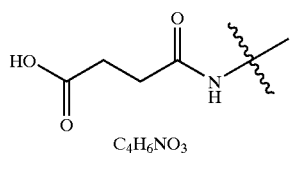 C₈H₉ | H | H |  C₄H₆NO₃ | H | Me | 473 | 0.0035 | 0.954 | 0.183 |
| 242 | CO₂Me | 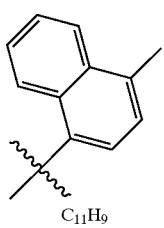 C₁₁H₉ | H | H | 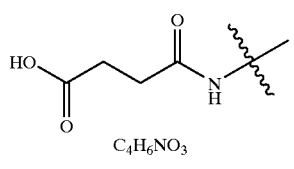 C₄H₆NO₃ | H | Me | 509 | 0.0038 | 0.782 | 0.141 |

TABLE 2-continued
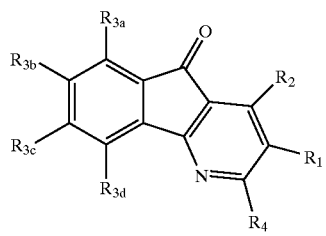
| No. | R₁ | R₂ | R₃ₐ | R₃ᵦ | R₃c | R₃d | R₄ | MS (M+1) | IC₅₀ (μM)/% inh. @ μM PDE7A | PDE4 | PDE5 |
|---|---|---|---|---|---|---|---|---|---|---|---|
| 243 | CO₂Me | C₄H₉ (isobutyl) | H | H | H | H | Me | 310 | 2.6 | | |
| 245 | CO₂Me | C₈H₉ (3,5-dimethylphenyl) | H | H | C₄H₇N₂O₃ (HONH-CO-CH₂CH₂-CO-NH-) | H | Me | 488 | 0.0053 | 0.875 | 0.185 |
| 248 | CO₂Me | Cyclohexyl | H | H | H | H | Me | 336 | 0.783 | 0.171 | 0.649 |
| 250 | CO₂Me | C₈H₉ (3,5-dimethylphenyl) | H | H | C₄H₉N₂O₂ (HOCH₂CH₂-NH-CH₂-CO-NH-) | H | Me | 474 | 0.0074 | 0.684 | 2.4 |
| 251 | CO₂Me | C₈H₉ (3,5-dimethylphenyl) | H | H | C₅H₈NO₃ (HOOC-CH₂CH₂-CH₂-CO-NH-) | H | Me | 487 | 0.0054 | 0.754 | 0.26 |
| 253 | CO₂Me | C₅H₁₀N (cyclopentyl-NH-) | H | H | H | H | Me | 337 | 0.905 | 0.85 | 0.303 |

TABLE 2-continued

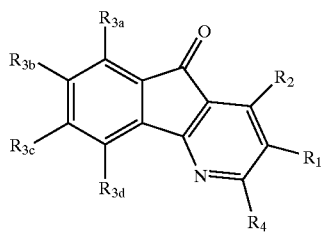

Ia

| No. | R₁ | R₂ | R₃ₐ | R₃ᵦ | R₃c | R₃d | R₄ | MS (M + 1) | IC₅₀ (μM)/% inh. @ μM PDE7A | PDE4 | PDE5 |
|---|---|---|---|---|---|---|---|---|---|---|---|
| 254 | $CO_2Me$ | 3,5-dimethylphenyl ($C_8H_9$) | H | H | $HOCH_2CH_2N(Me)CH_2C(O)NH-$ ($C_5H_{11}N_2O_2$) | H | Me | 488 | 0.0067 | 0.664 | 0.765 |
| 261 | $CO_2Me$ | 3,5-dimethylphenyl ($C_8H_9$) | H | H | morpholino-$CH_2C(O)NH-$ ($C_6H_{11}N_2O_2$) | H | Me | 500 | 0.0063 | 0.477 | 0.63 |
| 262 | $CO_2Me$ | 3,5-dimethylphenyl ($C_8H_9$) | H | H | piperazino-$CH_2C(O)NH-$ ($C_6H_{12}N_3O$) | H | Me | 499 | 0.008 | 0.702 | 3.7 |

What is claimed is:

1. A compound having the structure

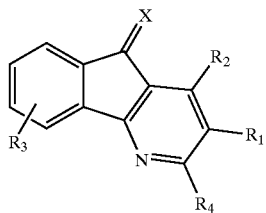

(a) $R_1$ is selected from the group consisting of:
  (i) —$COR_5$, wherein $R_5$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl,;
  (ii) $COOR_6$, wherein $R_6$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
  (iii) cyano;
  (iv) a lactone or lactam formed with $R_4$;
  (v) —$CONR_7R_8$ wherein $R_7$ and $R_8$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, and aryl;
    wherein the alkyl, cycloalkyl, alkoxy, acyl, alkylcarbonyl, carboxyl, arylalkyl, and aryl groups may be substituted with carboxyl, alkyl, aryl, substituted aryl, hydroxamic acid, sulfonamide, sulfonyl, hydroxy, thiol, alkoxy or arylalkyl, (b) $R_2$ is selected from the group consisting of optionally substituted alkyl, optionally substituted aryl, optionally substituted heterocyclyl, wherein the heterocyclyl is 1,3-dioxolane heterocylyl is 1,3-dixolane, and optionally substituted $C_{3-7}$ cycloalkyl, or $R_2$ is

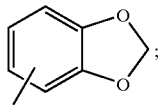;

(c) $R_3$ is from one to four groups independently selected from the group consisting of:
   (i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, and aryl;
   (ii) —$NR_{10}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, or aryl;
   (iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxyalkyl, $R_{30}R_{31}N(CH_2)_p$—, $R_{30}R_{31}NCO(CH_2)_p$—, aryl, and arylalkyl, wherein $R_{30}$ and $R_{31}$ are independently selected from H, OH, alkyl, and alkoxy, and p is an integer from 1–6, (d) $R_4$ is selected from the group consisting of (i) hydrogen, (ii) $C_{1-3}$ straight or branched chain alkyl, (iii) benzyl and (iv) —$NR_{13}R_{14}$, wherein $R_{13}$ and $R_{14}$ are independently selected from hydrogen and $C_{1-6}$ alkyl; wherein the $C_{1-3}$alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, and aryl; and (e) X is selected from S and O;
with the proviso that when $R_4$ is isopropyl, then $R_3$ is not halogen, and that when $R_4$ is $C_{1-3}$ straight or branched chain alkyl, then X is not O, $R_3$ is not H and $R_1$ is not COO-methyl and $R_2$ is not 2-methoxyphenyl, and the pharmaceutically acceptable salts, esters and pro-drug forms thereof.

2. The compound of claim 1, wherein $R_1$ is $COOR_6$, wherein $R_6$ is selected from H, optionally substituted $C_{1-8}$ straight or branched chain alkyl, optionally substituted aryl and optionally substituted arylalkyl.

3. The compound of claim 2, wherein $R_6$ is selected from H, or $C_{1-8}$ straight or branched chain alkyl which may be optionally substituted with a substituent selected from CN and hydroxy.

4. The compound of claim 1, wherein $R_2$ is optionally substituted aryl.

5. The compound of claim 4 wherein the aryl group is substituted with one to five members selected from the group consisting of halogen, alkyl, alkoxy, alkoxyphenyl, halo, triflouromethyl, trifluoro or difluoromethoxy, amino, alkylamino, hydroxy, cyano, and nitro.

6. The compound of claim 1 wherein, $R_2$ is optionally substituted phenyl, or napthyl or $R_2$ is

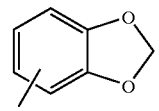

optionally substituted, wherein the optional substituents are from one to three members selected from the group consisting of halogen, alkyl, hydroxy, cyano, and nitro.

7. The compound of claim 1 wherein $R_3$ is selected from:
   (i) hydrogen, halo, $C_{1-8}$ straight or branched chain alkyl, $C_{1-8}$ alkoxy, cyano, $C_{1-4}$ carboalkoxy, trifluoromethyl, $C_{1-8}$ alkylsulfonyl, halogen, nitro, and hydroxy;
   (ii) —$NR_{10}R_{11}$ wherein $R_{10}$ and $R_{11}$ are independently selected from H, $C_{1-8}$ straight or branched chain alkyl, aryl$C_{1-8}$alkyl, $C_{3-7}$ cycloalkyl, carboxy$C_{1-8}$alkyl, or aryl;
   (iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxy$C_{1-8}$alkyl, aryl, arylalkyl, $R_{30}R_{31}N(CH_2)_p$—, or $R_{30}R_{31}NCO(CH_2)_p$—, wherein, $R_{30}$ and $R_{31}$ are independently selected from H, OH, alkyl, and alkoxy, and p is an integer from 1–6.

8. The compound of claim 7, wherein $R_3$ is selected from the group consisting of:

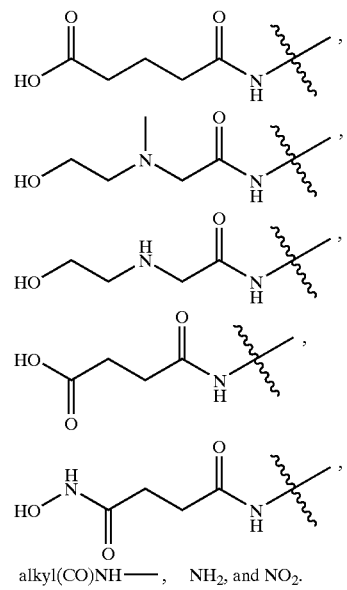

alkyl(CO)NH—, $NH_2$, and $NO_2$.

9. The compound of claim 1 wherein $R_4$ is selected from hydrogen, and $C_{1-3}$ straight or branched chain alkyl.

10. The compound of claim 9, wherein $R_4$ is selected from methyl and amino.

11. The compound of claim 1 wherein $R_1$ is $COOR_6$ and $R_2$ is selected from the group consisting of substituted phenyl, and substituted naphthyl.

12. The compound of claim 1 wherein $R_1$ is $COOR_6$ where $R_6$ is alkyl, $R_2$ is substituted phenyl or naphthyl, and $R_3$ is selected from the group consisting of H, nitro, amino, NHAc, halo, hydroxy, alkoxy, or a moiety of the formulae:

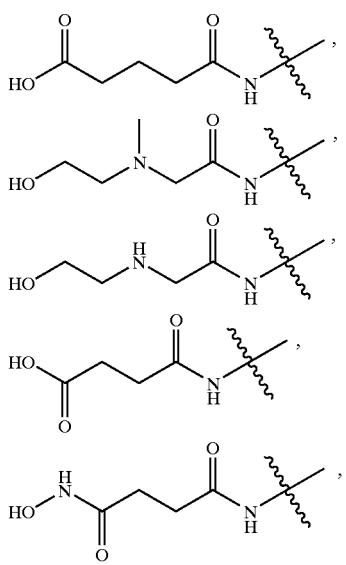

alkyl(CO)NH—, and R$_4$ is selected from hydrogen, C$_{1-3}$ straight or branched chain alkyl and amino and X is Oxygen.

13. A compound having the structure:

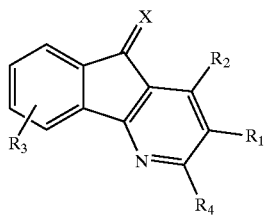

Formula I wherein
(a) R$_1$ is selected from the group consisting of:
(i) —COR$_5$, wherein R$_5$ is selected from H, optionally substituted C$_{1-8}$ straight or branched chain alkyl, optionally substituted aryl and optionally substituted arylalkyl;
wherein the substituents on the alkyl, aryl and arylalkyl group are selected from C$_{1-8}$ alkoxy, phenylacetyloxy, hydroxy, halogen, p-tosyloxy, mesyloxy, amino, cyano, carboalkoxy, or NR$_{20}$R$_{21}$ wherein R$_{20}$ and R$_{21}$ are independently selected from the group consisting of hydrogen, C$_{1-8}$ straight or branched chain alkyl, C$_{3-7}$ cycloalkyl, benzyl, or aryl;
(ii) COOR$_6$, wherein R$_6$ is selected from H, optionally substituted C$_{1-8}$ straight or branched chain alkyl, optionally substituted aryl and optionally substituted arylalkyl;
wherein the substituents on the alkyl, aryl and arylalkyl group are selected from C$_{1-8}$ alkoxy, phenylacetyloxy, hydroxy, halogen, p-tosyloxy, mesyloxy, amino, cyano, carboalkoxy, or NR$_{20}$R$_{21}$ wherein R$_{20}$ and R$_{21}$ are independently selected from the group consisting of hydrogen, C$_{1-8}$ straight or branched chain alkyl, C$_{3-7}$ cycloalkyl, benzyl, or aryl;
(iii) cyano;
(iv) a lactone or lactam formed with R$_4$;
(v) —CONR$_7$R$_8$ wherein R$_7$ and R$_8$ are independently selected from H, C$_{1-8}$ straight or branched chain alkyl, C$_{3-7}$ cycloalkyl, trifluoromethyl, hydroxy, alkoxy, acyl, alkylcarbonyl, carboxyl, arylalkyl, or aryl;
wherein the alkyl, cycloalkyl, alkoxy, acyl, alkylcarbonyl, carboxyl, arylalkyl, aryl, heteroaryl and heterocyclyl groups may be substituted with carboxyl, alkyl, aryl, substituted aryl, hydroxamic acid, sulfonamide, sulfonyl, hydroxy, thiol, alkoxy or arylalkyl;

(b) R$_2$ is —NR$_{15}$R$_{16}$ wherein R$_{15}$ and R$_{16}$ are independently selected from hydrogen, optionally substituted C$_{1-8}$ straight or branched chain alkyl, arylalkyl, C$_{3-7}$ cycloalkyl, aryl; with the proviso that when R$_2$ is NHR$_{16}$, R$_1$ is not —COOR$_6$ where R$_6$ is ethyl;

(c) R$_3$ is from one to four groups independently selected from the group consisting of:
(i) hydrogen, halo, C$_{1-8}$ straight or branched chain alkyl, arylalkyl, C$_{3-7}$ cycloalkyl, C$_{1-8}$ alkoxy, cyano, C$_{1-4}$ carboalkoxy, trifluoromethyl, C$_{1-8}$ alkylsulfonyl, halogen, nitro, hydroxy, trifluoromethoxy, C$_{1-8}$ carboxylate, or aryl;
(ii) —NR$_{10}$R$_{11}$ wherein R$_{10}$ and R$_{11}$ are independently selected from H, C$_{1-8}$ straight or branched chain alkyl, arylalkyl, C$_{3-7}$ cycloalkyl, carboxyalkyl, or aryl;
(iii) —NR$_{12}$COR$_{13}$ wherein R$_{12}$ is selected from hydrogen or alkyl and R$_{13}$ is selected from hydrogen, alkyl, substituted alkyl, C$_{1-3}$alkoxyl, carboxyalkyl, R$_{30}$R$_{31}$N(CH$_2$)$_p$—, R$_{30}$R$_{31}$NCO(CH$_2$)$_p$—, aryl, arylalkyl, heteroaryl and heterocyclyl or R$_{12}$ and R$_{13}$ taken together with the carbonyl form a carbonyl containing heterocyclyl group, wherein, R$_{30}$ and R$_{31}$ are independently selected from H, OH, alkyl, and alkoxy, and p is an integer from 1–6, wherein the alkyl group may be substituted with carboxyl, alkyl, aryl, substituted aryl, hydroxamic acid, sulfonamide, sulfonyl, hydroxy, thiol, alkoxy or arylalkyl;

(d) R$_4$ is selected from the group consisting of (i) hydrogen, (ii) C$_{1-3}$ straight or branched chain alkyl, (iii) benzyl and (iv) —NR$_{13}$R$_{14}$, wherein R$_{13}$ and R$_{14}$ are independently selected from hydrogen and C$_{1-6}$ alkyl; wherein the C$_{1-3}$alkyl and benzyl groups are optionally substituted with one or more groups selected from C$_{3-7}$ cycloalkyl, C$_{1-8}$ alkoxy, cyano, C$_{1-4}$ carboalkoxy, trifluoromethyl, C$_{1-8}$ alkylsulfonyl, halogen, nitro, hydroxy, trifluoromethoxy, C$_{1-8}$ carboxylate, amino, NR$_{13}$R$_{14}$, or aryl; and (e) X is selected from S and O; provided that when R$_4$ is C$_{1-3}$ straight or branched chain alkyl, then X is not O, R$_3$ is not H and R$_1$ is not COO— methyl and R$_2$ is not 2-methoxyphenyl, and the pharmaceutically acceptable salts, esters and pro-drug forms thereof.

14. The compound of claim 13, wherein R$_1$ is COOR$_6$ wherein R$_6$ is alkyl, R$_2$ is NR$_6$R$_7$, and R$_3$ is selected from the group consisting of

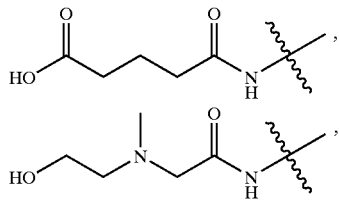

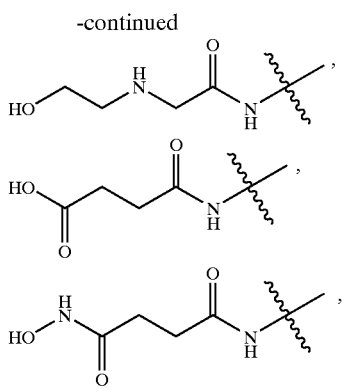

alkyl(CO)NH—, $NH_2$, $NO_2$, halogen, and hydrogen, and $R_4$ is selected from hydrogen, $C_{1-3}$ straight or branched chain alkyl and amino and X is Oxygen.

15. The compound of claim 1, which is 5H-indeno[1,2-b]pyridine-3-carboxylic acid, 4-(3,5-dimethylphenyl)-2-methyl-5-oxo-, methyl ester.

16. The compound of claim 1, which is 5H-indeno[1,2-b]pyridine-3-carboxylic acid, 8-(acetylamino)-4-(1,3-benzodioxol-5-yl)-2-methyl-5-oxo-, ethyl ester.

17. The compound of claim 1, which is 5H-indeno[1,2-b]pyridine-3-carboxylic acid, 7-amino-4-(3,5-dimethylphenyl)-2-methyl-5-oxo-, methyl ester.

18. The compound of claim 1, which is 5H-indeno[1,2-b]pyridine-3-carboxylic acid, 7-amino-2-methyl-4-(4-methyl-1-naphthalenyl)-5-oxo-, methyl ester.

19. The compound of claim 1, which is 5H-indeno[1,2-b]pyridine-3-carboxylic acid, 4-(3,5-dibromo-4-hydroxyphenyl)-2-methyl-8-nitro-5-oxo-, methyl ester.

20. The compound of claim 1, which is 5H-indeno[1,2-b]pyridine-3-carboxylic acid, 7,8-dichloro-4-(3,5-dibromo-4-hydroxyphenyl)-2-methyl-5-oxo-, methyl ester.

21. The compound of claim 1, which is 5H-indeno[1,2-b]pyridine-3-carboxylic acid, 8-[(3-carboxy-1-oxopropyl)amino]-4-(3,5-dimethylphenyl)-2-methyl-5-oxo-, methyl ester.

22. The compound of claim 1, which is 5H-indeno[1,2-b]pyridine-3-carboxylic acid, 8-[(3-carboxy-1-oxopropyl)amino]-2-methyl-4-(4-methyl-1-naphthalenyl)-5-oxo-, methyl ester.

23. The compound of claim 1, which is 5H-indeno[1,2-b]pyridine-3-carboxylic acid, 4-(3,5-dimethylphenyl)-8-[[4-(hydroxyamino)-1,4-dioxobutyl]amino]-2-methyl-5-oxo-, methyl ester.

24. The compound of claim 1, which is 5H-indeno[1,2-b]pyridine-3-carboxylic acid, 4-(3,5-dimethylphenyl)-8-[[[(2-hydroxyethyl)amino]acetyl]amino]-2-methyl-5-oxo-, methyl ester.

25. The compound of claim 1, which is 5H-indeno[1,2-b]pyridine-3-carboxylic acid, 8-[(4-carboxy-1-oxobutyl)amino]-4-(3,5-dimethylphenyl)-2-methyl-5-oxo-, methyl ester.

26. The compound of claim 1, which is 5H-indeno[1,2-b]pyridine-3-carboxylic acid, 4-(3,5-dimethylphenyl)-8-[[[(2-hydroxyethyl)methylamino]acetyl]amino]-2-methyl-5-oxo-, methyl ester.

27. The compound of claim 1, which is 5H-indeno[1,2-b]pyridine-3-carboxylic acid, 2-amino-4-(1,3-benzodioxol-5-yl)-5-oxo-, ethyl ester.

28. The compound of claim 1, which is 5H-indeno[1,2-b]pyridine-3-carboxylic acid, 4-(6-bromo-1,3-benzodioxol-5-yl)-2-methyl-5-oxo-, ethyl ester.

29. The compound of claim 1, which is 5H-indeno[1,2-b]pyridine-3-carboxylic acid, 7-amino-4-(1,3-benzodioxol-5-yl)-2-methyl-5-oxo-, ethyl ester.

30. The compound of claim 1, which is 5H-indeno[1,2-b]pyridine-3-carboxylic acid, 4-(6-bromo-1,3-benzodioxol-5-yl)-2-methyl-5-oxo-, methyl ester.

31. The compound of claim 1, which is 5H-indeno[1,2-b]pyridine-3-carboxylic acid, 2-methyl-4-(3-methylphenyl)-5-oxo-, methyl ester.

32. The compound of claim 1, which is 5H-indeno[1,2-b]pyridine-3-carboxylic acid, 7-bromo-4-(3,5-dibromo-4-hydroxyphenyl)-2-methyl-5-oxo-, methyl ester.

33. The compound of claim 1, which is 5H-indeno[1,2-b]pyridine-3-carboxylic acid, 8-bromo-4-(3,5-dibromo-4-hydroxyphenyl)-2-methyl-5-oxo-, methyl ester.

34. A pharmaceutical composition comprising the compound of claim 1 and a pharmaceutically acceptable carrier.

35. A pharmaceutical composition comprising the compound of claim 13 and a pharmaceutically acceptable carrier.

* * * * *